US010255990B2

(12) United States Patent
Apte et al.

(10) Patent No.: US 10,255,990 B2
(45) Date of Patent: Apr. 9, 2019

(54) METHOD AND SYSTEM FOR FRAGMENT ASSEMBLY AND SEQUENCE IDENTIFICATION

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US); Rodrigo Ortiz, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 0 days.

(21) Appl. No.: 15/811,544

(22) Filed: Nov. 13, 2017

(65) Prior Publication Data

US 2018/0137240 A1    May 17, 2018

Related U.S. Application Data

(60) Provisional application No. 62/424,843, filed on Nov. 21, 2016, provisional application No. 62/420,733, filed on Nov. 11, 2016.

(51) Int. Cl.
*G06F 19/22* (2011.01)
*C12N 15/10* (2006.01)
(Continued)

(52) U.S. Cl.
CPC .......... *G16B 30/00* (2019.02); *C12N 15/1065* (2013.01); *C12N 15/1093* (2013.01);
(Continued)

(58) Field of Classification Search
None
See application file for complete search history.

(56) References Cited

U.S. PATENT DOCUMENTS

| 4,683,195 A | 7/1987 | Mullis et al. |
| 7,323,305 B2 | 1/2008 | Leamon et al. |
| (Continued) | | |

OTHER PUBLICATIONS

Adey, A. et al. In vitro, long-range sequence information for de novo genome assembly via transposase contiguity. Genome Research 24, 2041-2049 (2014).*
(Continued)

*Primary Examiner* — Soren Harward
(74) *Attorney, Agent, or Firm* — Kilpatrick Townsend & Stockton LLP

(57) ABSTRACT

Embodiments of a method and/or system for improving fragment assembly and/or sequence identification includes: collecting a sample including a set of nucleic acid components associated with a set of microorganisms; generating a set of tagged sequence fragments; amplifying the set of tagged sequence fragments and sequencing the set of tagged sequence fragments; based upon the set of identifier tags, generating a set of branched assemblies of candidate sequence fragments, wherein each of the set of branched assemblies includes a set of ordered nodes and a set of branches distributed across the set of nodes; implementing a threshold criterion to reduce the set of branched assemblies to a set of branch-reduced assemblies; and identifying a set of sequences corresponding to the set of branch-reduced assemblies and/or generating an analysis informative of the set of microorganisms associated with the sample.

14 Claims, 14 Drawing Sheets

(51) Int. Cl.
*C12Q 1/6869* (2018.01)
*G16B 30/00* (2019.01)
*C40B 50/06* (2006.01)

(52) U.S. Cl.
CPC ............ *C40B 50/06* (2013.01); *C12Q 1/6869* (2013.01); *C12Q 2600/156* (2013.01)

(56) References Cited

U.S. PATENT DOCUMENTS

| | | | |
|---|---|---|---|
| 8,003,330 B2 | 8/2011 | Heiner et al. | |
| 9,663,831 B2 | 5/2017 | Apte et al. | |
| 9,703,929 B2 | 7/2017 | Apte et al. | |
| 9,710,606 B2 | 7/2017 | Apte et al. | |
| 9,754,080 B2 | 9/2017 | Apte et al. | |
| 9,758,839 B2 | 9/2017 | Apte et al. | |
| 9,760,676 B2 | 9/2017 | Apte et al. | |
| 10,073,952 B2 | 9/2018 | Apte et al. | |
| 2005/0124010 A1 | 6/2005 | Short et al. | |
| 2006/0024681 A1* | 2/2006 | Smith | C12P 19/34 435/6.18 |
| 2009/0024555 A1 | 1/2009 | Rieck et al. | |
| 2010/0069263 A1* | 3/2010 | Shendure | C12N 15/1093 506/26 |
| 2011/0015096 A1* | 1/2011 | Chiu | C12N 15/1093 506/16 |
| 2012/0208705 A1* | 8/2012 | Steemers | C12N 15/1065 506/2 |
| 2013/0079231 A1* | 3/2013 | Pushkarev | C12Q 1/6874 506/2 |
| 2013/0203605 A1* | 8/2013 | Shendure | C12N 15/1093 506/2 |
| 2015/0211078 A1 | 7/2015 | Apte et al. | |
| 2016/0208241 A1* | 7/2016 | Tsai | C40B 50/06 |
| 2016/0224749 A1 | 8/2016 | Apte et al. | |
| 2016/0228003 A1 | 8/2016 | Apte et al. | |
| 2016/0232319 A1 | 8/2016 | Apte et al. | |
| 2016/0259909 A1 | 9/2016 | Apte et al. | |
| 2016/0362748 A1 | 12/2016 | Mongan et al. | |
| 2017/0024527 A1 | 1/2017 | Apte et al. | |
| 2017/0053061 A1 | 2/2017 | Almonacid et al. | |
| 2017/0058339 A1 | 3/2017 | Chee | |
| 2017/0267997 A1* | 9/2017 | Nicol | C12N 15/1065 |

OTHER PUBLICATIONS

Bankevich, A. & Pevzner, P. A. TruSPAdes: Barcode assembly of TruSeq synthetic long reads. Nature Methods 13, 248-250 (2016).*
Caruccio, N. Preparation of Next-Generation Sequencing Libraries Using NexteraTM Technology: Simultaneous DNA Fragmentation and Adaptor Tagging by In Vitro Transposition. Chapter 17 of High-Throughput Next Generation Sequencing (eds. Kwon, Y. M. & Ricke, S. C.) 241-255 (Humana Press, 2011).*
Hiatt, J. B., Patwardhan, R. P., Turner, E. H., Lee, C. & Shendure, J. Parallel, tag-directed assembly of locally derived short sequence reads. Nature Methods 7, 119-122 (2010).*
Kuleshov, V., Snyder, M. P. & Batzoglou, S. Genome assembly from synthetic long read clouds. Bioinformatics 32, i216-i224 (2016).*
Lan, F., Haliburton, J. R., Yuan, A. & Abate, A. R. Droplet barcoding for massively parallel single-molecule deep sequencing. Nature Communications 7, 1-10 (2016).*
Marine, R. et al. Evaluation of a transposase protocol for rapid generation of shotgun high-throughput sequencing libraries from nanogram quantities of DNA. Applied and Environmental Microbiology 77, 8071-8079 (2011).*
McCoy, R. C. et al. Illumina TruSeq synthetic long-reads empower de novo assembly and resolve complex, highly-repetitive transposable elements. PLoS ONE 9, (2014).*
Oulas, A. et al. Metagenomics: Tools and insights for analyzing next-generation sequencing data derived from biodiversity studies. Bioinformatics and Biology Insights 9, 75-88 (2015).*
Picelli, S. et al. Tn5 transposase and tagmentation procedures for massively scaled sequencing projects. Genome Research 24, 2033-2040 (2014).*
Syed, F., Grunenwald, H. & Caruccio, N. Optimized library preparation method for next-generation sequencing. Nature Methods 6, I-II (2009).*
Wajid, B. & Serpedin, E. Review of General Algorithmic Features for Genome Assemblers for Next Generation Sequencers. Genomics, Proteomics and Bioinformatics 10, 58-73 (2012).*
Meyer, M., Stenzel, U., Myles, S., Prüfer, K. & Hofreiter, M. Targeted high-throughput sequencing of tagged nucleic acid samples. Nucleic Acids Research 35, e97:1-5 (2007).*
Parameswaran, P. et al. A pyrosequencing-tailored nucleotide barcode design unveils opportunities for large-scale sample multiplexing. Nucleic Acids Research 35, e130:1-9 (2007).*
Hernandez et al., "De Novo Bacterial Genome Sequencing: Millions of Very Short Reads Assembled on a Desktop Computer", Genome Research, vol. 18, No. 5, May 2008, pp. 802-809.
PCT/US2017/061404, "International Search Report and Written Opinion", dated Apr. 23,2018, 11 pages.

\* cited by examiner

METHOD AND SYSTEM FOR FRAGMENT ASSEMBLY AND SEQUENCE IDENTIFICATION

CROSS-REFERENCE TO RELATED APPLICATIONS

This application claims the benefit of U.S. Provisional Application Ser. No. 62/424,843 filed 21 Nov. 2016 and U.S. Provisional Application serial number 62/420,733 filed 11 Nov. 2016, each of which is herein incorporated in its entirety by this reference.

TECHNICAL FIELD

This invention relates generally to the field of molecular diagnostics and more specifically to a new and useful method and system for fragment assembly and sequence identification in the field of molecular diagnostics.

BACKGROUND

Processes involving amplification, detection, and analysis of nucleic acid targets within a sample can be used for sample characterization and/or diagnostic testing in research or clinical environments. Amplification, detection, and analysis of multiple nucleic acid targets are thus particularly useful in characterizing multiple sample components and or enabling diagnostics associated with multiple targets (e.g., health condition biomarkers). Current methods and systems for multiplexed amplification, detection, sequencing, and/or analysis of multiple nucleic acid targets in a high throughput manner are, however, subject to limitations in terms of fragment assembly and sequence identification, especially in the context of highly polymorphic sequences.

Multiplexed amplification, detection, sequencing, and/or analysis of multiple nucleic acid targets is also typically limited by the number of reactions that can be performed within a single system (e.g., process chamber). Furthermore, current methods of multiplex sample processing are time consuming, labor intensive, and can be prohibitively expensive to implement.

As such, there is a need in the field of molecular diagnostics for a new and useful method and system for fragment assembly and sequence identification. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview.

Figure 1A:
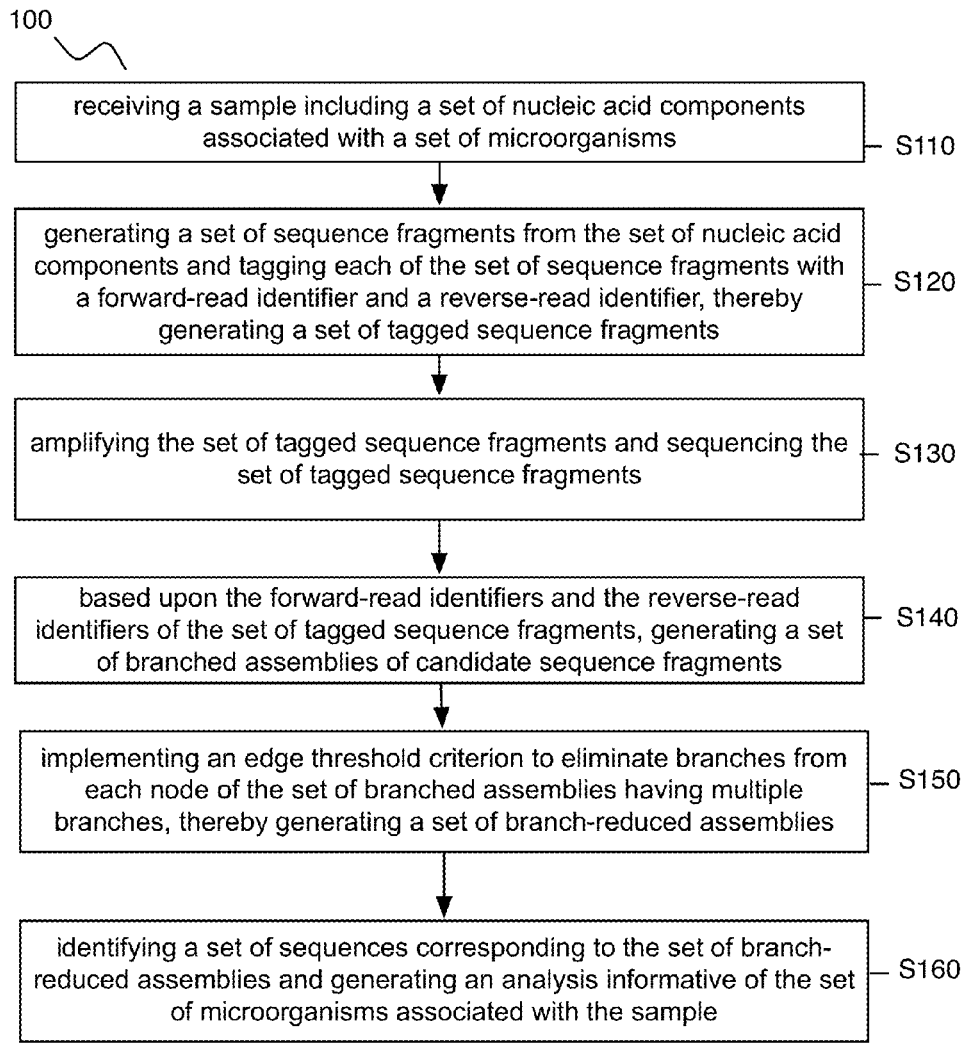
FIGS. 1A-1B are schematic representation of embodiments of a method for fragment assembly and sequence identification.
Figure 1B:
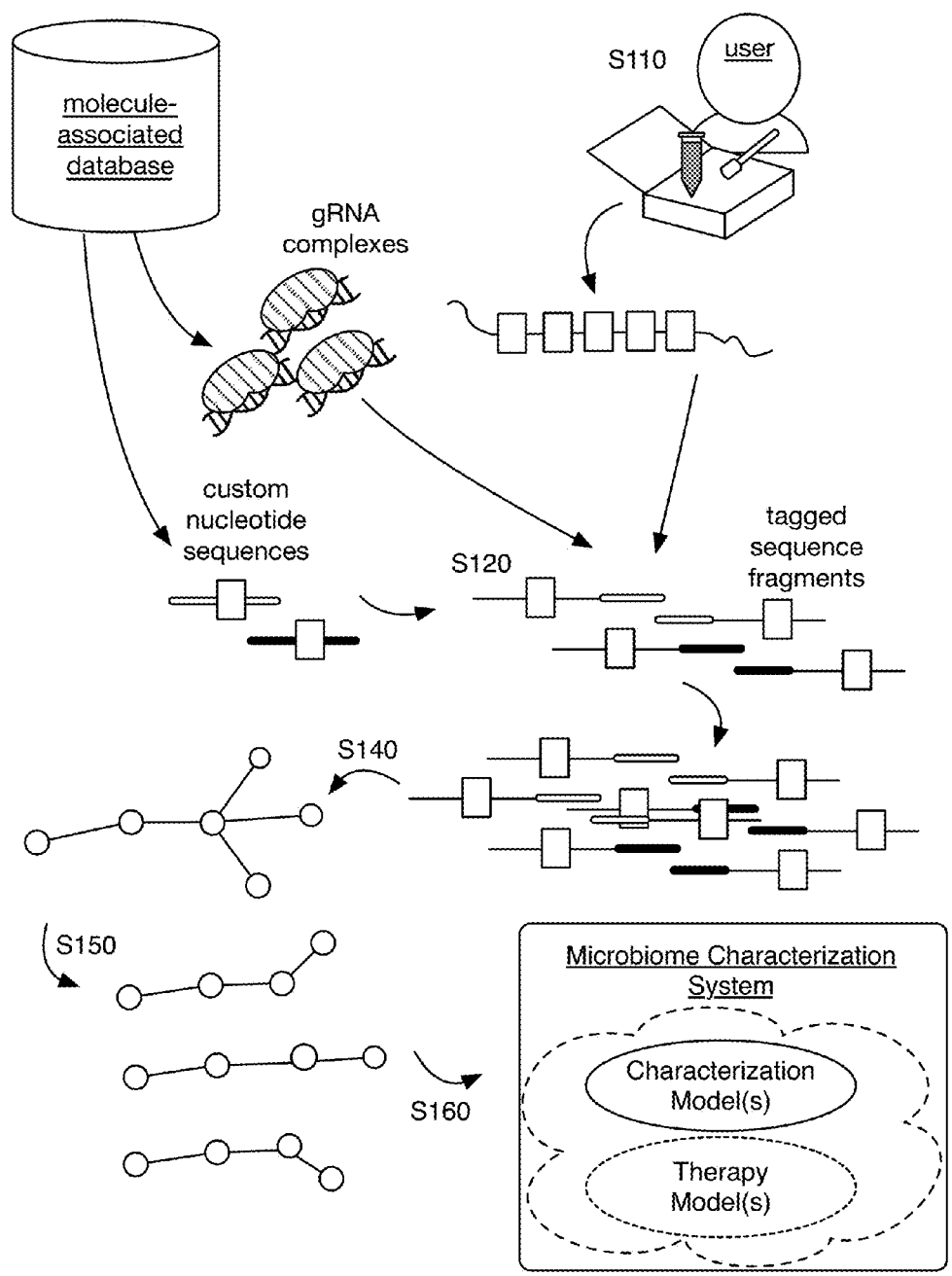

As shown in FIGS. 1A-1B, embodiments of a method 100 for improving fragment assembly and/or sequence identification (e.g., in relation to a set of microorganism) includes: collecting a sample including a set of nucleic acid components associated with a set of microorganisms S110; generating a set of sequence fragments from the set of nucleic acid components and tagging each of the set of sequence fragments with a set of identifier tags (e.g., forward-read identifier and/or a reverse-read identifier, etc.), thereby generating a set of tagged sequence fragments S120; amplifying the set of tagged sequence fragments and sequencing the set of tagged sequence fragments S130; based upon the set of identifier tags associated with (e.g., included in, etc.) the set of tagged sequence fragments, generating a set of branched assemblies of candidate sequence fragments S140, where each of the set of branched assemblies includes a set of ordered nodes and a set of branches distributed across the set of nodes; implementing a threshold criterion (e.g., an edge threshold criterion) to reduce (e.g., eliminate, etc.) the set of branched assemblies (e.g., reduce branches from each node of the set of branched assemblies having multiple branches, etc.) to a set of branch-reduced assemblies S150; and identifying a set of sequences (e.g., microorganism sequences, etc.) corresponding to the set of branch-reduced assemblies and/or generating an analysis (e.g., microbiome analysis) informative of the set of microorganisms associated with the sample S160.

Embodiments of the method 100 and/or system 200 can function to enable improved assembly and identification of a mixture of nucleic acid sequences of organisms (e.g., microorganisms, etc.) present in one or more biological sample, where the sequences can be associated with highly polymorphic regions. In a specific example, embodiments can facilitate assembly and/or mapping of nucleic acids that have been fragmented prior to assembly (e.g., for amplification), where the nucleic acids can be from a set of different types of organisms present in a biological sample. In a specific example, embodiments can be used to assemble fragments of the highly polymorphic v4 region of 16S rRNA and/or any other suitable target regions (e.g., target sequence regions). However, variations can additionally or alternatively be configured to enable assembly and/or identification of any other suitable target sequence region (e.g., other 16S rRNA region, 18S rRNA sequence region, ITS sequence region, sequence regions(s) of other genetic markers, sequence region(s) of other phylogenetic markers, etc.). In other examples, guide RNA (gRNA) complexes (e.g., high efficiency gRNA complexes, etc.) can be used in facilitating generation of sequence fragments associated with identifier tags for facilitating subsequent assembly and mapping and/or other suitable portions of the method 100 and/or system 200, where the gRNA complexes can include and/or be used for targeting any one or more of: gRNA sequences, PAM sites, other locator sites, V4 regions, restriction enzyme sites, and/or other suitable components. Embodiments can include any one or more of: generating sequence fragments from a set of microorganism nucleic acid components based on processing with a set of gRNA complexes; ligating, for the sequence fragments, a first set of identifier tags and restriction sites; performing a first circularization operation with the sequence fragments; digesting the sequence fragments with a first set of restriction enzymes; ligating with a second set of identifier tags and restriction sites; performing a second circularization operation; digesting with a second set of restriction enzymes; repeating any of the processes described herein in any suitable order; and/or performing any other suitable operations. Additional or alternative processing operations (e.g., end repair; phosphorylation, such as with T4 kinase; ligation of adapter sequences for facilitating sequencing; repetition of processing operations; etc.) can be used in combination with, prior to, after, and/or at any suitable time in relation to other portions of the method 100.

Additional or alternative variations can be used to enable assembly of fragments of a mixture of any other suitable element types.

In examples, embodiments of the method 100and/or system 200 can improve fragment assembly and/or sequence identification for facilitating generation and/or promotion of characterizations and/or therapies for a condition and/or panel of conditions, where conditions can include one or more of: symptoms, causes, diseases, disorders, microbiome pharmacogenomics profiles (e.g., describing resistance and/or susceptibility to antibiotics) and/or any other suitable aspects associated with conditions. Conditions can include one or more of: gut-related conditions; psychiatric and behavioral conditions (e.g., a psychological disorder; depression; psychosis; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); a cardiovascular-related condition (e.g., coronary artery disease; high blood pressure; etc.); metabolic-related conditions (e.g., diabetes, etc.), rheumatoid-related conditions (e.g., arthritis, etc.); weight-related conditions (e.g., obesity, etc.); pain-related conditions; endocrine-related conditions; genetic-related conditions; chronic disease; and/or any other suitable type of conditions. Gut-related conditions can include any one or more of: diarrhea, irritable bowel syndrome (IBS), inflammatory bowel disease (IBD), Crohn's Disease, ulcerative colitis, constipation, abdominal tenderness, bloating, flatulence, obesity, type II diabetes, prediabetes, kidney stones, cardiovascular health, and anxiety, other suitable gut conditions, and/or any suitable conditions.

In variations, portions of the method 100 can be repeatedly performed in any suitable order to enable refining of assembly-related and/or sequence identification-related processes (e.g., refining of models used to assemble branch assemblies, reduce branch assemblies, identify microorganism sequences based on branch-reduced assemblies; refining molecule-associated databases for identification and/or selection of custom nucleotide molecules, cutting sties, identifier tags, guide RNAs, associated proteins for guide RNA complexes; linkers; and/or other suitable molecules described herein; etc.) and/or other suitable processes.

Additionally or alternatively, parameters, metrics, inputs, outputs, and/or other suitable data can be associated with value types including: scores (e.g., similarity scores for branch-reduction processes; other score metrics for branch-reduction processes; confidence scores for correspondences between branch-reduced assemblies and microorganism sequences; microbiome diversity scores; risk scores for conditions; etc.), binary values (e.g., presence or absence of branches at a node for a branched assembly; presence or absence of a microbiome feature; presence or absence of a condition; etc.), classifications (e.g., taxonomic group classifications for microorganism sequences; selection of a branch of a set of candidate branches for branch-reduction processes; condition-related classifications; behavioral classifications based on the microbiome analysis; demographic classifications; etc.), confidence levels (e.g., associated with microorganism sequence datasets; with microbiome diversity scores; with other headache-related characterizations; etc.), values along a spectrum, and/or any other suitable types of values. Any suitable types of data described herein can be used as inputs (e.g., for different models described herein), generated as outputs (e.g., of different models), and/or manipulated in any suitable manner for any suitable components associated with the method 100 and/or system 200.

Additionally or alternatively, data described herein (e.g., branch assemblies; branch-reduced assemblies; branch reduction models; other suitable models; microorganism sequence data; microbiome features; microbiome analyses; population-level data; user-level data; treatment-related data; etc.) can be associated with any suitable temporal indicators (e.g., seconds, minutes, hours, days, weeks, etc.; temporal indicators indicating when the data was collected, determined and/or otherwise processed; temporal indicators providing context to content described by the data, such as temporal indicators indicating a branched assembly status at the time at which the biological sample was collected; etc.) and/or change in temporal indicators (e.g., microbiome composition over time; microbiome function over time; branched assembly status over time; and/or other suitable aspects over time; change in data; data patterns; data trends; data extrapolation and/or other prediction; etc.).

One or more instances of the method 100 and/or processes described herein can be performed asynchronously (e.g., sequentially), concurrently (e.g., in parallel; targeting, amplifying, assembling, and/or otherwise performing sequencing-related processes for a plurality of microorganism-related targets; multiplexing to enable processing of multiple biological samples in parallel, such as for a plurality of users; computationally assembling and/or reducing a plurality of branch assemblies for one or more samples, such as concurrently on different threads for parallel computing to improve system processing ability; etc.), in temporal relation to a trigger event, and/or in any other suitable order at any suitable time and frequency by and/or using one or more instances of the system (e.g., including a sample handling network, a panel characterization system, a therapy system, sample kits, etc.), elements, and/or entities described herein. Portions of the method 100 can be implemented at least in part at a computing system, where the computing system can be implemented in one or more of a computer, a workstation associated with an automated laboratory system, a semi-automated laboratory system, a remote server, a cloud-based computing system, a computing module of a mobile computing device, and any other suitable computing module. In variations, the method 100 can be implemented by at least components described in U.S. application Ser. No. 14/593, 424 entitled "Method and System for Microbiome Analysis" and filed on 9 Jan. 2015, which is herein incorporated in its entirety by this reference, and/or by any suitable components of a system 200.

Embodiments of the method 100 can be implemented by at least embodiments of a system 200 that can include: a sample handling system operable to process biological samples according to portions of the method 100 (e.g., generating, amplifying, and/or sequencing tagged sequence fragments; generating custom nucleotide molecules, linkers, and/or other suitable molecules for facilitating portions of the method 100; etc.); a microbiome characterization system (e.g., a computer system operable to determine microbiome characterizations based off of microorganism sequences derived from branch-reduced assemblies; etc.); a molecule-associated database (e.g., including design-factors, sequences, selections, and/or other suitable data associated with synthesis, application of, and/or other processing of molecules described herein; etc.); and/or any other suitable components. However, the method 100 and system 200 can be performed in any suitable manner.

2. Benefits.

Specific examples of the method 100 and/or system 200 can confer technologically-rooted solutions to challenges arising from conventional approaches.

First, the technology can confer improvements in improving fragment assembly and/or sequence identification in relation to microbiome analysis (e.g., for a plurality of microorganism targets; etc.); sample processing and sample analysis efficiency; computational processing speed; microbiome-related characterization accuracy; microbiome-related therapy determination and promotion, and/or other suitable aspects associated with the technical fields of microbiome sequencing and/or related sample preparation.

Second, the technology can transform entities (e.g., users, biological samples, nucleic acid components of microorganisms, treatment systems including medical devices, etc.) into different states or things. For example, the technology can transform nucleic acid components of a biological sample into a set of branched assemblies for identifying microorganism sequence data upon which microbiome analyses can be based (e.g., microbiome-related characterization for a microorganism-associated condition; etc.). In another example, the technology can leverage fragment assembly and/or sequence identification processes described herein to facilitate identification of therapies to promote to a patient to modify a microbiome composition, microbiome functional diversity, a microbiome pharmacogenomics profile and/or other microbiome-related aspects to prevent and/or ameliorate one or more microorganism-related conditions, thereby transforming the microbiome and/or health of the patient.

Third, the technology can amount to an inventive distribution of functionality across a network including a molecule-associated database, a sample handling system, a microbiome characterization system, and a plurality of users, where the sample handling system can handle substantially concurrent processing of biological samples (e.g., for facilitating determination of branched assemblies; etc.) for a plurality of microorganism targets, which can be leveraged by the microbiome characterization system (e.g., for processing branched assemblies into microbiome sequence datasets and subsequent microbiome analyses; etc.) in generating personalized microbiome characterizations and/or therapies (e.g., customized to the user's microbiome such as in relation to the user's dietary behavior, probiotics-associated behavior, medical history, demographics, other behaviors, preferences, etc.) for microorganism-related conditions.

Fourth, the technology can leverage specialized sample processing devices (e.g., next generation sequencing devices; CRISPR-related devices; mircobiome characterization systems; treatment systems; etc.) in performing portions of the method 100. The technology can, however, provide any other suitable benefit(s) in the context of using non-generalized systems for improved fragment assembly and/or sequence identification.

3.1 Collecting a Sample.

Block S110 recites: collecting a sample including a set of nucleic acid components (e.g., DNA, RNA, etc.) associated with a set of microorganisms (e.g., associated with a diversity of taxa, etc.), which functions to provide sample material that can be analyzed to determine sample composition (e.g., through performing other portions of the method 100; etc.). Block Siio preferably includes receiving a sample from a subject in a non-invasive manner. In variations, non-invasive manners of sample reception implemented in Block S110 can use any one or more of: a permeable substrate (e.g., a swab configured to wipe a region of a subject's body, toilet paper, a sponge, etc.), a non-permeable substrate (e.g., a slide, tape, etc.), a container (e.g., vial, tube, bag, etc.) configured to receive a sample from a region of a subject's body, and/or any other suitable sample-reception element. In a specific example, samples can be collected from one or more of a subject's nose, skin, genitals, mouth, and gut in a non-invasive manner (e.g., using a swab and a vial). However, one or more biological samples of the set of biological samples can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can include blood samples, plasma/serum samples (e.g., to enable extraction of cell-free DNA), cerebrospinal fluid, and/or tissue samples.

In some embodiments, receiving the sample in Block S110 can be performed according to embodiments, variations, and examples of sample reception as described in U.S. application Ser. No. 14/593,424 filed on 9 Jan. 2015 and entitled "Method and System for Microbiome Analysis", which is incorporated herein in its entirety by this reference. However, receiving the sample in Block S110 can additionally or alternatively be performed in any other suitable manner. Furthermore, some alternative variations of the first method 100 can omit Block S110, with processing of data derived from a sample performed as described below in subsequent blocks of the method 100.

3.2 Generating Tagged Sequence Fragments.

Block S120 recites: generating a set of sequence fragments from the set of nucleic acid components and tagging each of the set of sequence fragments with a set of identifier tags (e.g., forward-read identifiers and reverse-read identifiers; etc.), thereby generating a set of tagged sequence fragments. Block S120 can functions to generate appropriately-sized fragments for amplification and/or other suitable processing in Block S130 and/or other suitable portions of the method 100. Additionally or alternatively, Block S120 can function to tag fragments (e.g., including target sequence regions; etc.) and/or other suitable molecules (e.g., associated with target markers) with one or more identifier tags that can be used to facilitate downstream assembly processes according to portions of the method 100. In a specific example, Block S120 can include generating a set of tagged sequence fragments based on a set of identifier tags and a set of sequence fragments derived from one or more sets of nucleic acid components of one or more samples.

In Block S120, generating the set of fragments can include performing an amplification operation, which can include one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably designed to universally amplify all of the nucleic acid targets in the sample associated with the comprehensive diagnostic test. Additionally or alternatively, the primers can be selected to prevent or minimize amplification bias, as well as configured to amplify nucleic acid regions/sequences (e.g., of the 16S rRNA region, the 18S rRNA region, the ITS region, etc.) that are informative taxonomically, phylogenetically, for diagnostics, and/or for any other suitable purpose. Thus, universal primers configured to avoid amplification bias can be used in amplification. Additionally or alternatively, primers used in Block S120 can include degenerate primers and/or any other suitable primer types (e.g., associated with target sequence regions, associated with one or more taxa, associated with one or more conditions; etc.).

In one variation, generating the set of sequence fragments from the amplicons in Block S120 can include implementing Nextera™ technology or other methods of fragmenting nucleic acid sequences, to then perform a size selection operation to generate sequences of a desired size or range of sizes. In this variation, adjusting fragmentation process time (or other parameters) can be used to provide fragments of a desired size range for amplification. Additionally or alternatively, in another variation, other laboratory methods of fragmentation (e.g., mechanical), and size selection (e.g., chromatographic methods, electrophoretic methods, filtration methods, etc.) can be used to provide fragments of a desired size range for amplification. Fragmentation and size selection can, however, be implemented in Block S120 and/or other portions of the method 100 in any other suitable manner. In a specific example, Block S120 generates fragments on the order of 450 base pairs (bp); however, any other suitable fragment length (e.g., up to 1000 bp, greater than 1000 bp, within ranges of 5000 bp-6000 bp, 1000 bp-2500 bp, different fragment lengths depending on types of gRNA complexes used, type and/or number of digestion operations, etc.) can be generated in Block S120 and/or other suitable portions of the method 100.

Alternatively, in relation to generation of fragments in Block S120, fragments of different sizes (e.g., with a desired distribution in sizes) can be combined for amplification based upon binding efficiency (e.g., Illumina binding efficiency as a function of fragment length). In particular for a distribution of fragments (e.g., produced using a Nextera™ technology), fragments of different sizes can be combined in a manner that is associated with binding efficiency (e.g., proportional to, inversely proportional to); thus, fragments with low binding efficiency (e.g., long fragments) can have a specified abundance (e.g., lower abundance as proportional to binding efficiency, higher abundance as inversely proportional to binding efficiency) in a sample having a mixture of fragment lengths, and fragments with a high binding efficiency (e.g., shorter fragments) can have a specified abundance (e.g., higher abundance as proportional to binding efficiency, lower abundance as inversely proportional to binding efficiency) in a sample having a mixture of fragment lengths. Thus, downstream assembly steps of the method 100 can involve assembly of non-uniformly-lengthed sequences, in relation to a distribution of amplicon fragment sizes generated in Block S120. However, fragmentation to generate amplicon fragments can be performed in Block S120 in any other suitable manner. Furthermore, any fragmentation process can be performed with any suitable ligation process (e.g., in cooperation with tagging processes, in a separate process from tagging).

Figure 2:
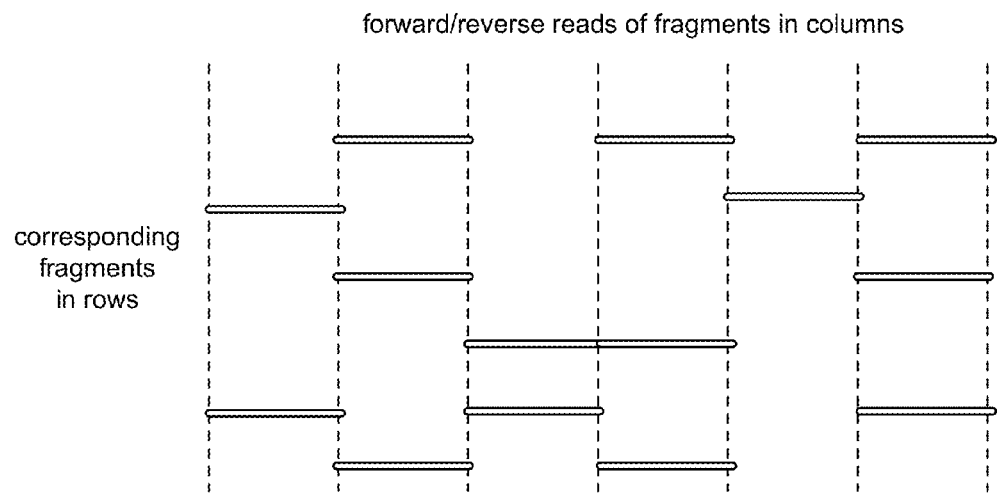
FIG. 2 depicts a variation of a portion of an embodiment of a method for fragment assembly and sequence identification.

In Block S120, tagging each of the set of sequence fragments with a forward-read identifier and a reverse-read identifier preferably includes tagging each fragment with a forward sequence tag and a reverse sequence tag. In relation to tagging, tagging facilitates identification of fragments corresponding to the same target, as shown in FIG. 2, where the fragments are processed to have a forward read sequence or a reverse read sequence upon sequencing using a suitable sequencing platform (e.g., Illumina sequencing, etc.). As such, tagging, in combination with sequencing, allows for efficient amplification and downstream sequencing and assembly, such that highly polymorphic assembled sequences can be distinguished from each other.

Block S120 preferably includes tagging one or more molecules associated with (e.g., including) one or more target markers (e.g., target markers associated with one or more microorganism taxonomic groups; functional aspects; conditions; user responsiveness to different therapies; markers invariant across a population and/or any suitable set of subjects; etc.). Target markers preferably include target sequences (e.g., associated with the generated sequence fragments; sequences to facilitate multiplex amplification using a primer type sharing a primer sequence; conserved sequences; sequences including mutations, polymorphisms; nucleotide sequences; amino acid sequences; etc.), but can additionally or alternatively include: proteins (e.g., serum proteins, antibodies, etc.), peptides, carbohydrates, lipids, other nucleic acids, whole cells, metabolites, natural products, genetic predisposition biomarkers, diagnostic biomarkers, prognostic biomarkers, predictive biomarkers, other molecular biomarkers, gene expression markers, imaging biomarkers, and/or other suitable markers.

In one variation, the identifier tags can be tags associated with Illumina technology; however, variations of Block S120 can additionally or alternatively include using any other suitable tagging technology. In one example, Block S120 can implement processing components (e.g., components that append tags to target amplicons). In one example, tagging can include implementing primers that append sequencing elements to the amplicon fragments in a manner that facilitates downstream assembly according to the method 100. In one example, in relation to Illumina sequencing, tagging can provide one or more of: a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region, a reverse index sequence (e.g., corresponding to an Illumina reverse index for MiSeq/NextSeq/HiSeq platforms), sequences associated with sequencing primers (e.g., for facilitating paried end sequencing on next generation sequencing systems; etc.) and, optionally, a reverse barcode sequence. Additionally or alternatively, any other suitable forward and/or reverse tagging components can be used in Block S120. However, Block S120 can be performed in any suitable manner.

3.3 Amplifying and/or Sequencing.

Block S130 recites: amplifying the set of tagged sequence fragments and/or sequencing the set of tagged sequence fragments, which can function to provide improved limits of detection (e.g., upon amplification), and/or to enable identification of sequences of fragments for downstream assembly of complete sequences (e.g., microorganism sequences; etc.) of regions of interest.

In Block S130 , amplifying preferably includes one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. Primers used in variations of Block S130 can additionally or alternatively include incorporated barcode sequences specific to each sample, which can facilitate identification of biological samples post-amplification. As indicated above, primers used in variations of Block S130 can additionally or alternatively include adaptor regions configured to cooperate with sequencing techniques involving complementary adaptors (e.g., Illumina Sequencing). Additionally or alternatively, primers used in Block S130 can include degenerate primers. Additionally or alternatively, Block S130 can implement any other step configured to facilitate processing, some embodiments, variations, and examples of which are described in as described in U.S. application Ser. No. 16/240,919 entitled "Method and System for Multiplex Primer Design" and filed on 18 Aug. 2016, which is herein incorporated in its entirety by this reference. However, primers can be associated with (e.g., complementary to sequences indicative of, etc.) any suitable targets, taxa, conditions, and/or other suitable components.

In Block S130, sequencing can implement techniques including one or more of: sequencing-by-synthesis techniques (e.g., Illumina sequencing), capillary sequencing techniques (e.g., Sanger sequencing), pyrosequencing techniques, nanopore sequencing techniques (e.g., using an Oxford Nanopore technique), or any other suitable sequencing technique. In a specific example, sequencing includes Illumina sequencing (e.g., with a HiSeq platform, with a MiSeq platform, with a NextSeq platform, etc.) using a sequencing-by-synthesis technique with a paired end sequencing approach (e.g., with forward and reverse reads), embodiments, variations, and examples of which are described in U.S. application Ser. No. 14/593,424 entitled "Method and System for Microbiome Analysis" and filed on 9 Jan. 2015. However, Block S130 can be performed in any suitable manner.

3.4 Generating Branched Assemblies.

Figure 3:
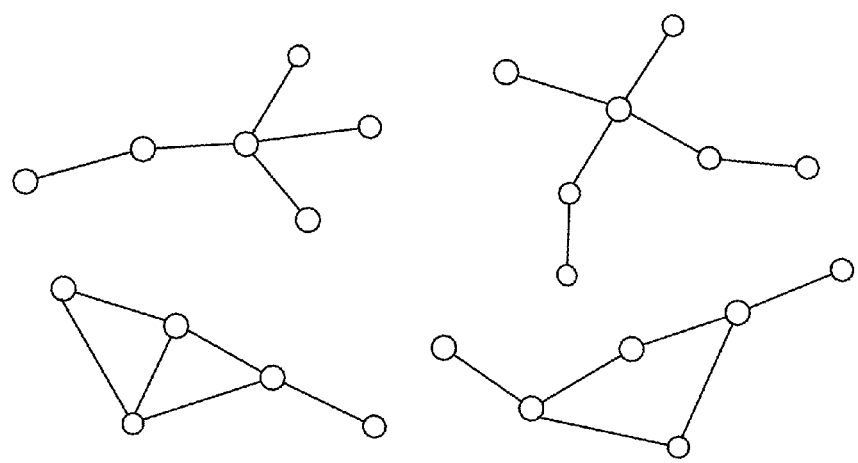
FIG. 3 depicts example branched assemblies generated in an embodiment of a method for fragment assembly and sequence identification.

Block S140 recites: based upon the set of identifier tags (e.g., forward-read identifiers, the reverse-read identifiers, etc.) of the set of tagged sequence fragments, generating a set of branched assemblies corresponding to candidate sequence fragments. Block S140 can function as an assembly operation sub-step that arranges sequenced fragments into a set of ordered branched assemblies, where a path from an initiating point of an assembly to a terminating point of the assembly can correspond to an actual assembled sequence. In more detail, each assembly generated in Block S140 can have a set of ordered nodes (e.g., ordered based upon sequence position) and a set of branches connecting the set of nodes, examples of which are shown in FIG. 3. In a specific example, Block S140 can include: generating a set of branched assemblies corresponding to candidate sequence fragments, based on a set of identifier tags associated with the sequenced set of tagged sequence fragments, where each branched assembly of the set of branched assemblies includes a set of branches distributed across a set of nodes.

Figure 4A:
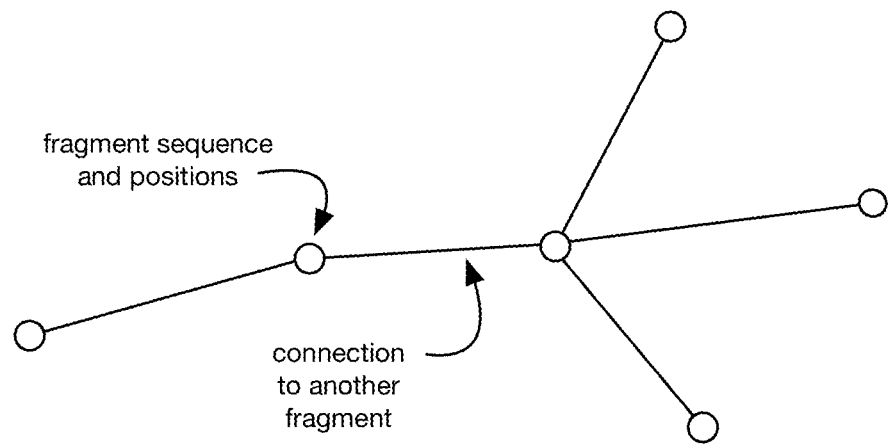
FIGS. 4A-4B depict variations of branched assembly element definitions and configurations.

As such, in generating the set of branched assemblies, each of the set of branched assemblies can include a set of ordered nodes and a set of branches distributed across the set of nodes, where each of the set of nodes can be coupled to at least one of the set of branches. In a variation, as shown in FIG. 4A, each node of the set of nodes corresponds to a sequenced fragment (e.g., microorganism sequenced fragment) having a length, an initiating position, and a terminating position, and where a connection between adjacent nodes indicates continuity or any other suitable correspondence between different sequence fragments (e.g., a candidate continuity between a plurality of microorganism sequenced fragments; etc.), where identifying the set of microorganisms (e.g., Block S160) and/or other portions of the method 100 (e.g., Block S150; etc.) can be based on lengths, initiating positions, terminating positions, connections between nodes and/or other suitable aspects of branched assemblies.

Figure 4B:
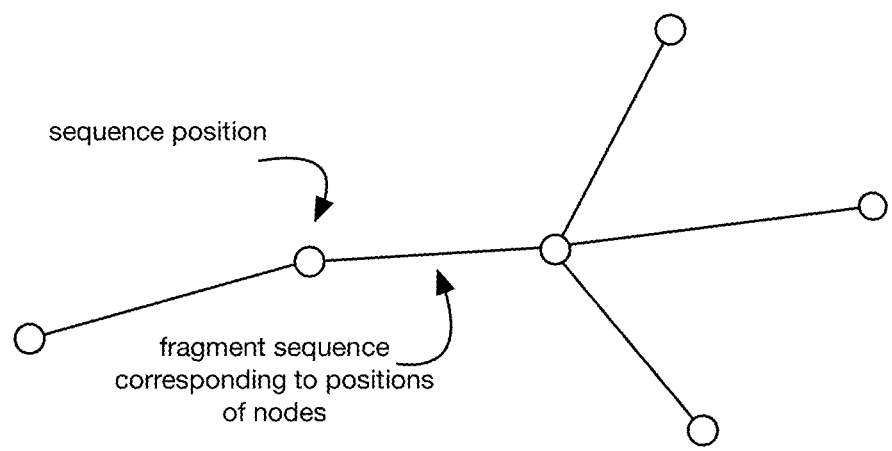

In another variation, as shown in FIG. 4B, each of the set of branched assemblies includes a set of ordered nodes and a set of branches distributed across the set of nodes, where each of the set of nodes is coupled to at least one of the set of branches, where each of the set of nodes corresponds to a position along an assembled sequence, and where each of the set of branches corresponds to a sequenced fragment including an initial position corresponding to an upstream node and a terminating position corresponding to a downstream node, where identifying the set of microorganisms (e.g., Block S160) and/or other portions of the method 100 (e.g., Block S150; etc.) can be based on initial positions, terminating positions, positions along assembled microorganism sequences, and/or any other suitable aspects of branched assemblies. However, the nodes, branches, and/or other suitable aspects associated with branched assemblies can be configured in any other suitable manner (e.g., in order to represent positions of candidate sequenced fragments and/or their relationships to each other; etc.).

Figure 5:
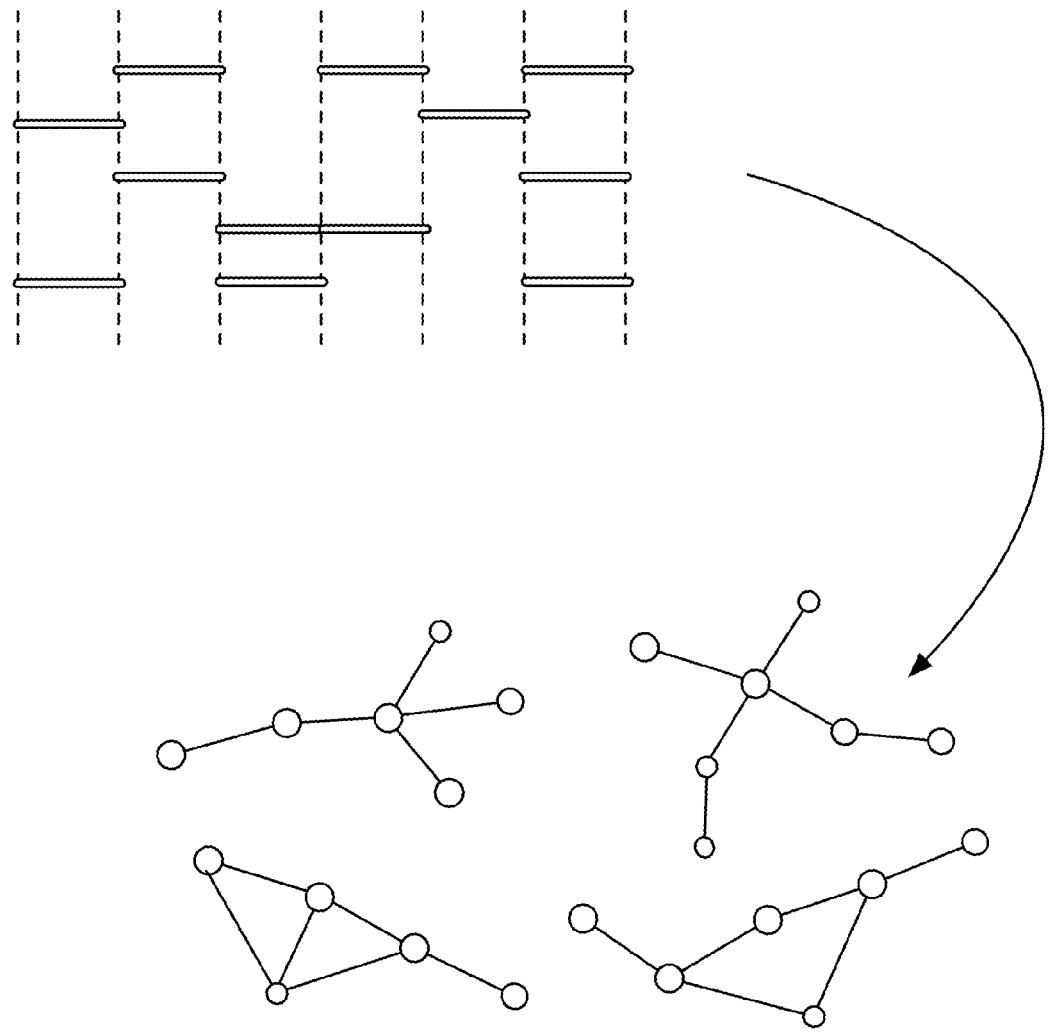
FIGS. 5-6 depict variations of portions of an embodiment of a method for fragment assembly and sequence identification.

As shown in FIG. 5, Block S140 can include identifying the forward fragment sequence reads and the reverse fragment sequence reads post-sequencing in Block S130 , and based on detection of the identifier tag(s) post-sequencing, generating the set of branched assemblies by aggregating, at each node/sequence position, an arrangement of fragment sequence candidates corresponding to each node. In particular, labeling the amplicon(s) at both ends, according to the method 100, can facilitate assembly post-sequencing in relation to both forward reads and reverse reads. Block S140 can include generating a graphical representation of each branched assembly (e.g., within a graphical user interface), examples of which are shown in FIG. 3; however, Block S140 can additionally or alternatively represent the branched assemblies in any other suitable manner (e.g., based upon "coordinate positions" of branches/nodes, etc.). In a variation, the method 100 can include receiving a user input associated with one or more branched assemblies (e.g., a user input inputted from a user in response to presenting the branched assemblies to the user at the user interface; etc.). User inputs can include one or more of: user preferences (e.g., for parameters to be optimized, such as confidence scores, in relation to portions of the method 100, such as confidence scores for a branch-reduced assembly corresponding to a particular microorganism sequence; etc.); inputs upon which parameter values can be determined (e.g., similarity coefficients; threshold criteria; etc.); inputs facilitating portions of the method 100 (e.g., inputs for reducing branches of branch assemblies; etc.); and/or any other suitable types of user inputs. In a specific example, the method 100 can include: generating a graphical representation of the set of branched assemblies (e.g., based on the set of branches and the set of nodes); presenting the graphical representation of the set of branched assemblies (e.g., to a user at a web application, at a mobile device, at another user interface; etc.); collecting a user input associated with the set of branched assemblies (e.g., in response to presenting the graphical representation of the set of branched assemblies; etc.); and implementing the threshold criterion to reduce the set of branched assemblies to the set of branch-reduced assemblies based on the user input (e.g., where the user input includes a selection of a threshold criterion; where values of the threshold criterion can be determined based on the user input; etc.). However, presenting branched assemblies and/ or other suitable data described herein, and/or collecting and/or using user inputs can be performed in any suitable manner.

In relation to uniformly-sized fragments, Block S140 can generate branched assemblies, where each branch can have a a uniform characteristic length corresponding to the fragment length (e.g., 50 base pairs, 30 base pairs, any other suitable number of base pairs); however, in relation to non-uniformly-sized fragments, Block S140 can additionally or alternatively generate assemblies having non-uniformly-sized branches. In variations of Block S140, sequence fragments preferably include fragments that have endpoints corresponding to node positions; however, alternative variations of Block S140 can include assembling sequence fragments having endpoints not corresponding to node positions. For instance, variations of Block S140 can include truncating identified sequences, such that the endpoints of each sequence correspond to adjacent node positions of a branched assembly.

Furthermore, the identifier tags can be used in Block S140 to perform processes associated with validation of the fragmentation process (e.g., Nextera fragmentation process). For instance, identification of identifier sequences during sequencing can be indicative of parameters associated with one or more of: amplification efficiency, proper fragmentation (e.g., generation of appropriately-sized fragments), and/ or any other suitable parameter able to be identified for any other suitable identification techniques available and applicable to the present technology. However, Block S140 can be performed in any suitable manner.

3.5 Generating Branch-Reduced Assemblies.

Block S150 recites: implementing a threshold criterion (e.g., an edge threshold criterion) and/or other suitable conditions to reduce (e.g., eliminate, etc.) the set of branched assemblies (e.g., reduce branches from each node having multiple branches, etc.) to a set of branch-reduced assemblies. Block S150 can function to reduce the number of candidate branches/connections associated with different nodes (e.g., node positions), such that an identified sequence can be extracted for each branched assembly (e.g., with above a threshold degree of confidence, etc.). In a specific example, Block S150 can include: for the each branched assembly of a set of branched assemblies, applying the threshold criterion for each node coupled to branches of the set of branches (e.g., nodes where branching occurs, indicating multiple possible candidate sequences for the branch assemblies; etc.) to generate an unbranched assembly.

Preferably, Block S150 includes implementing a threshold condition for each node (e.g., each node edge) that results in elimination of branches/connections between nodes until an unbranched assembly remains. In this variation, the unbranched assembly can thus correspond to an actual assembled sequence, corresponding to an organism component of the sample being processed. Alternatively, implementation of the threshold condition can function to reduce a highly branched assembly to an assembly with a significantly reduced amount of branching, from which an actual assembled sequence can be determined using another suitable method.

Figure 6:
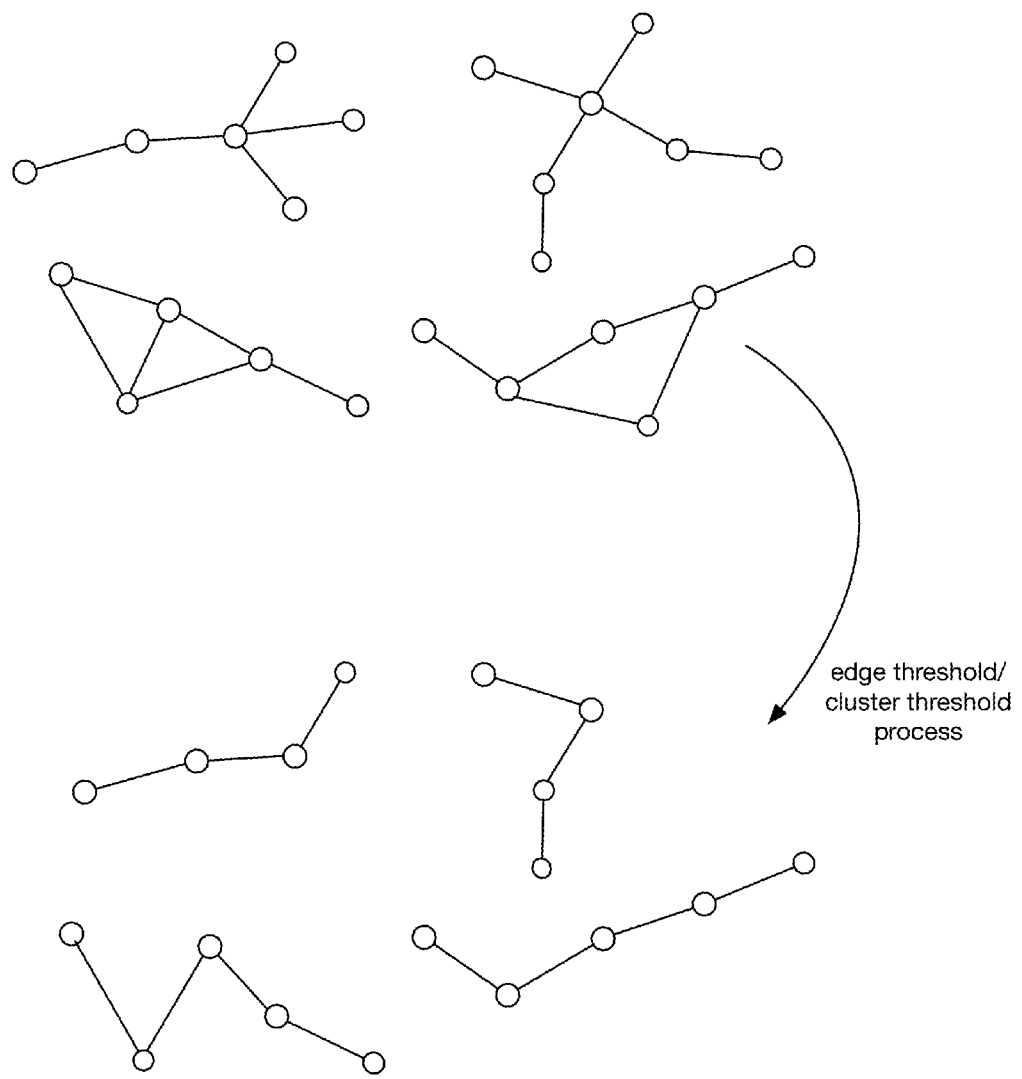

In one variation, Block S150 includes implementation of an edge threshold and/or cluster threshold criteria that facilitates elimination of connections between nodes of the branched assemblies. In this variation, the edge threshold/ cluster threshold criteria implements a similarity coefficient that compares similarity/diversity of sample sets associated with the branched assemblies, in terms of a parameter related to the union between the sample sets and a parameter related to the intersection between sample sets. As such, Block S150 can produce a set of branch-reduced assemblies from the set of branched assemblies, as shown in FIG. 6. In a specific example, Block S150 can include implementing one or more similarity coefficients for the set of branches and the set of nodes to reduce the set of branched assemblies to the set of branch-reduced assemblies.

In a specific example, Block S150 implements a Tanimoto Coefficient equal to the size of the intersection divided by the size of the union between sample sets. However, variations of Block S150 can use any other suitable similarity coefficients or distance parameters in reducing the number of branches between nodes of the branched assemblies, including one or more of: a Jaccard distance parameter; a Sorensen similarity index; a simple matching coefficient; a Mountford's index of similarity; a Hamming distance; a Dice's coefficient; a Tversky index; a Mutual information parameter; and any other suitable similarity, dissimilarity, or distance parameter.

Implementing the edge thresholding criterion can be performed across the set of branched assemblies simultaneously, with substantially similar criteria across each of the set of branched assemblies to produced assemblies having a reduction in branching. In an additional or alternative variation, the edge thresholding process can be performed in stages, with increasing stringency in tested criteria for each branched assembly, in order to generate assemblies having a reduction in branching. In the alternative variation, the criteria for generating the branch-reduced assemblies may differ across the set of branch-reduced assemblies. However, Block S150 can alternatively be implemented in any other suitable manner (e.g., where different branch-reduction processes can be performed based on type of targets, biological samples, collection sites, users, conditions, optimization parametres, and/or any other suitable conditions; etc.).

In relation to Block S150, each branched assembly can be associated with a set of candidate assembled sequences (e.g., prior to implementation of the edge thresholding process).

Figure 7:
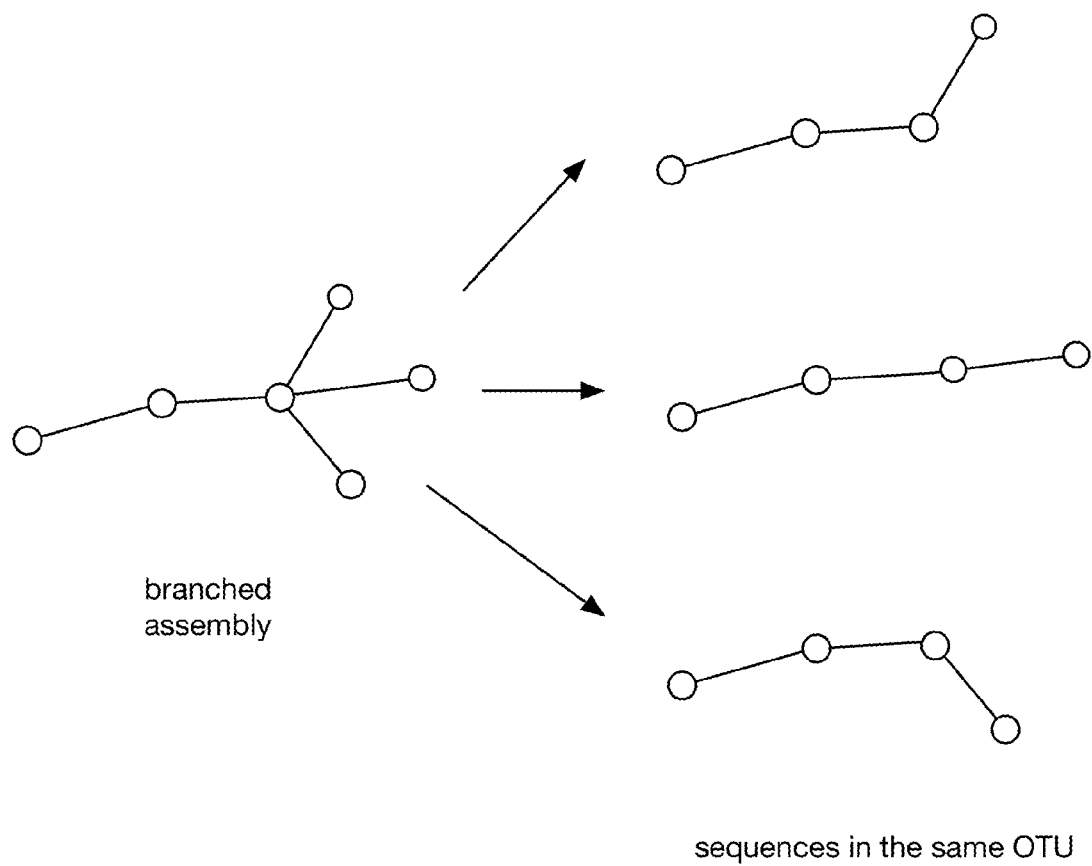
FIG. 7 depicts an example of defining operational taxonomic units using a method for fragment assembly and sequence identification.

In a variation, the set of candidate assembled sequences can correspond to an operational taxonomic unit, as shown in FIG. 7, such that Block S150 includes defining an operational taxonomic unit (OTU) from (e.g., based on; etc.) the set of candidate assembled sequences corresponding to a particular branched assembly. Block S150 can, however, include extracting any other suitable information relevant and/or useful for further procedures, and/or can be performed in any suitable manner.

3.6 Identifying Microorganism Sequences.

Block S160 recites: identifying a set of sequences (e.g., microorganism sequences, etc.) corresponding to the set of branch-reduced assemblies; and/or generating a microbiome analysis (e.g., microbiome composition diversity analysis; microbiome feature diversity analysis; etc.) informative of the set of microorganisms associated with the sample. Block S160 can function to provide an analysis of the microbiome compositional makeup of the sample, in terms of the type, abundance information, and/or functional features of microorganisms present in the sample. Block S160 preferably includes, for each branch-reduced assembly: translating the final set of nodes and/or branches into a sequence, and identifying an organism corresponding to the sequence. The organisms corresponding to the sequences can be defined at any suitable taxonomic level including one or more of: a kingdom, a phylum, a class, an order, a family, a genus, a species, and subspecies level, and/or any other taxonomic level.

As indicated above, Block S160 can additionally or alternatively include determining abundance parameters from the set of sequences, where abundance parameters determined in Block S160 can include raw abundance parameters (e.g., with a normalization factor) or relative abundance parameters.

Block S160 can additionally or alternatively include determining functional features associated with the set of sequences of the sample, where determining functional features can, in some variations, include extracting functional feature information from relevant databases, based on the set of sequences identified in Block S160. In some variations, to determine the set of functional features corresponding to sequences of the sample, Block S160 can include performing a search of at least one or more databases, such as the Kyoto Encyclopedia of Genes and Genomes (KEGG) and/or the Clusters of Orthologous Groups (COGs) database managed by the National Center for Biotechnology Information (NCBI). Searching can be performed based upon the set of sequences. In more detail, Block S160 can include implementation of a data-oriented entry point to a KEGG database including one or more of a KEGG pathway tool, a KEGG BRITE tool, a KEGG module tool, a KEGG ORTHOLOGY (KO) tool, a KEGG genome tool, a KEGG genes tool, a KEGG compound tool, a KEGG glycan tool, a KEGG reaction tool, a KEGG disease tool, a KEGG drug tool, a KEGG medicus tool, Searching can additionally or alternatively be performed according to any other suitable filters. Additionally or alternatively, Block S160 can include implementation of an organism-specific entry point to a KEGG database including a KEGG organisms tool. Additionally or alternatively, Block S160 can include implementation of an analysis tool including one or more of: a KEGG mapper tool that maps KEGG pathway, BRITE, or module data; a KEGG atlas tool for exploring KEGG global maps, a BlastKOALA tool for genome annotation and KEGG mapping, a BLAST/FASTA sequence similarity search tool, and a SIMCOMP chemical structure similarity search tool, and/or using any other suitable tool available for similar purposes.

In specific examples, Block S160 can include extracting functional features, using the set of sequences identified post-assembly, from a KEGG database resource and a COG database resource; however, Block S160 can additionally or alternatively include extracting candidate functional features using any other suitable database or set in any other suitable manner. For instance, Block S160 can include extracting candidate functional features, including functional features derived from a Gene Ontology functional classification, and/or any other suitable features for functional classification of sequences/genes.

Sequences, microbiome composition information, microbiome functional information, and/or any other suitable information extracted in Block S160 can be used to generate characterization models, diagnostics, and/or therapeutic models for treating different health conditions, embodiments, variations, and examples of which are described in U.S. application Ser. No. 15/097,862, titled "Method and System For Microbiome-Derived Diagnostics and Therapeutics for Neurological Health Issues" and filed on 13 Apr. 2016, which is herein incorporated in its entirety by this reference. However, Block S160 can be performed in any suitable manner.

4. Method 200.

Figure 8A:
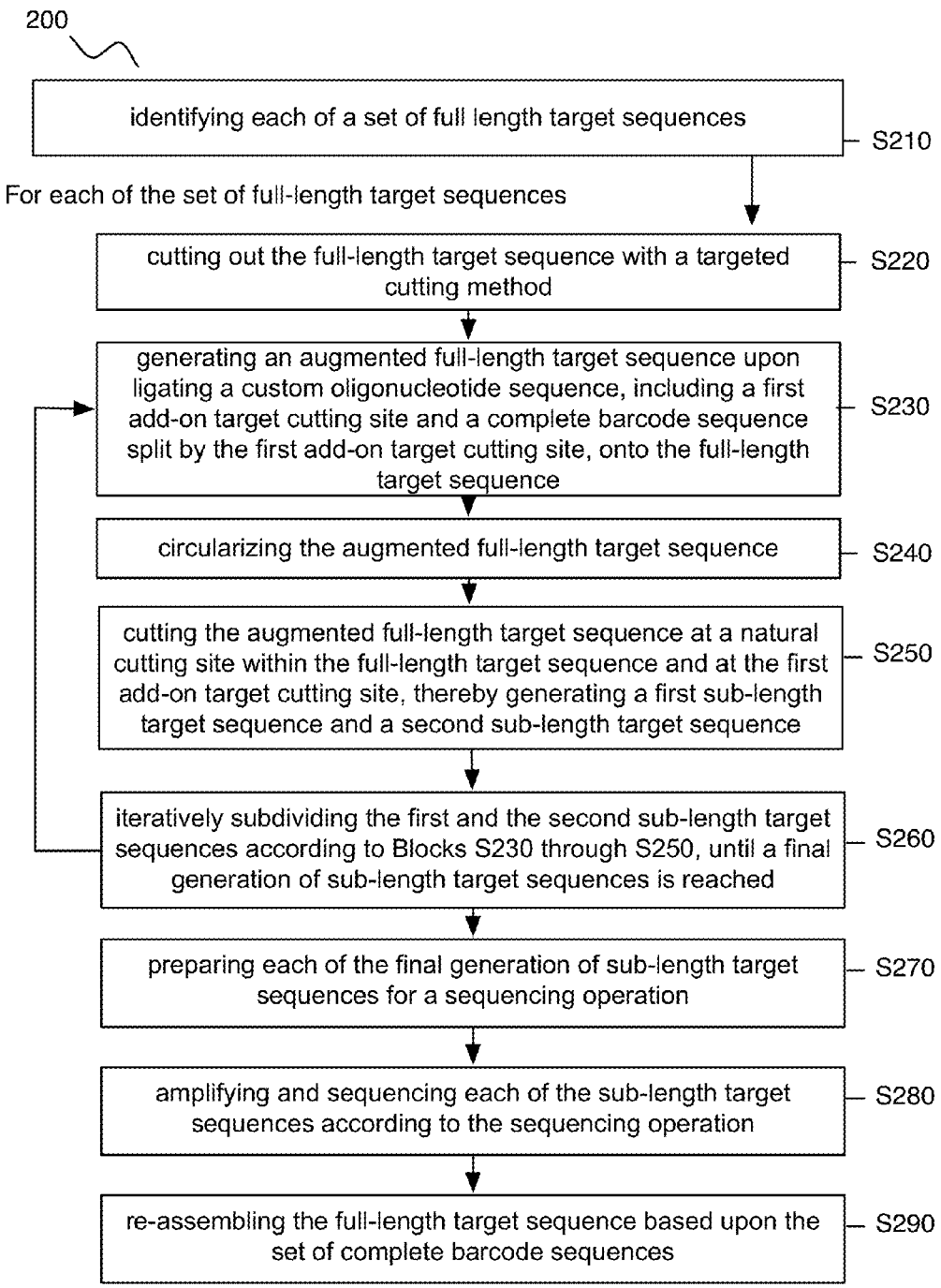
FIGS. 8A-8B depict embodiments of a second method for sequencing and assembly of full-length target sequences.
Figure 8B:
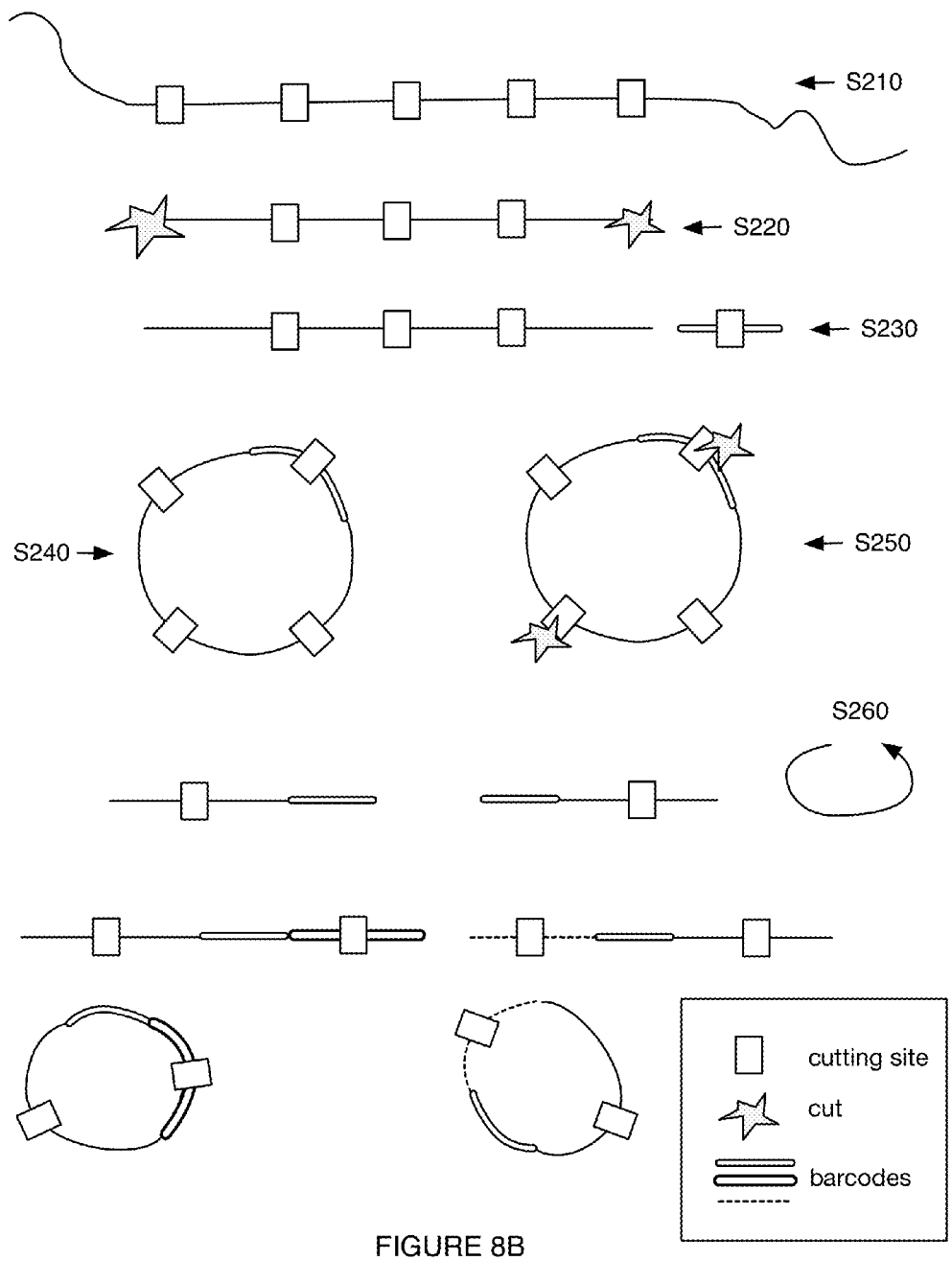

The method 100 can additionally or alternatively include portions of embodiments of a method 200 (e.g., where embodiments of the method 100, method 200, and/or method 300 can apply any suitable processes described in relation to method 100, method 200, and/or method 300 in any suitable combination; etc.) for assembling and/or sequencing fragments (e.g., longer fragments; etc.) of nucleic acid sequences, where, as shown in FIGS. 8A and 8B. Embodiments of the method 200 can include: identifying each of a set of full length target sequences S210; for each full-length target sequence identified: cutting out the full-length target sequence with a targeted cutting method S220; generating an augmented full-length target sequence upon ligating a custom oligonucleotide sequence, including a first add-on target cutting site and a complete barcode sequence split by the first add-on target cutting site, onto the full-length target sequence S230; circularizing the augmented full-length target sequence S240; cutting the augmented full-length target sequence at a natural cutting site within the full-length target sequence and at the first add-on target cutting site, thereby generating a first sub-length target sequence and a second sub-length target sequence, the first and the second sub-length target sequences associated with each other by including sequences that form the complete barcode sequence S250 ; iteratively subdividing the first and the second sub-length target sequences according to Blocks S230 through S250, until a final generation of sub-length target sequences is reached, where each of the final generation of sub-length target sequences has a length below a threshold sequencing length and includes a subportion of a set of complete barcode sequences implemented in Block S230 and iterations of Block S260; preparing each of the final generation of sub-length target sequences for a sequencing operation S270; amplifying and sequencing each of the sub-length target sequences according to the sequencing operation S280; and re-assembling the full-length target sequence based upon the set of complete barcode sequences S290. Specific examples can include generating a set of custom nucleotide molecules including cutting sites and identifier tags, where the set of custom nucleotide molecules is associated with microorganism target sequences; collecting a sample including a set of nucleic acid components associated with the set of microorganisms; generating augmented full-length target sequence fragments from the set of nucleic acid components based on processing the sample with the set of custom nucleotide molecules; generating sub-length target sequence fragments associated with the identifier tags, based on the cutting sites of the set of custom nucleotide molecules; and performing a sequence operation based on the sub-length target sequence fragments, thereby generating a microorganism sequence dataset; and determining a microbiome analysis corresponding to the set of microorganisms based on the microorganism sequence dataset and the set of identifier tags associated with the sub-length target sequence fragments.

The method 200 can function to enable accurate assembly of fragmented sequences of target sequences (e.g., long target sequences having 5000 bases or greater, sequences having hundreds of bases, sequences having thousands of bases, other sequences with any suitable size; etc.) based on existing cutting sites in the target sequences, and can reduce the computational difficulty of solving downstream assembly of sequenced fragments with a novel upstream wet-lab sample processing approach. Similar to the method 100, the method 200 can function to enable sequencing and assembly of one or more nucleic acid sequences of organisms present in a biological sample (e.g., in a mixture), where the sequences are associated with highly polymorphic regions. In a specific example, the method 200 can be used to assemble fragments of the highly polymorphic v4 region of 16S rRNA. However, variations of the method 200 can additionally or alternatively be configured to enable assembly and identification of any other suitable sequence region (e.g., other 16S rRNA region, 18S rRNA sequence region, ITS sequence region, sequence regions(s) of other genetic markers, sequence region(s) of other phylogenetic markers, etc.). Still alternative variations of the method 200 can be used to enable assembly of fragments of a mixture of any other suitable element types.

Block S210 recites: identifying each of a set of full length target sequences, which can function to locate positions of target sequences within genomes of organism targets in a sample. Block S210 preferably includes identifying starting position of each full length target sequence and a terminating position of each full length target sequence. In relation to naturally-occurring locator sites associated with cutting sites (e.g., protospacer adjacent motifs, PAMs) within the genomes, Block S210 can additionally or alternatively include identifying the locator site(s) closest to the starting position and the terminating position of each full-length target sequence. In relation to Block S210, the PAM site(s) can have one or more of the following sequences: 5'-NGA-3'; 5'-NGG-3'; 5'-TTN-3'; 5'-YTN-3'; and any other suitable PAM sequence.

Block S210 preferably includes identifying the relevant positions associated with the highly polymorphic v4 region of 16S rRNA. However, variations of Block S210 can additionally or alternatively include identifying the relevant positions associated with any other suitable region (e.g., other 16S rRNA region, 18S rRNA sequence region, ITS sequence region, sequence regions(s) of other genetic markers, sequence region(s) of other phylogenetic markers, etc.). However, Block S210 can be performed in any suitable manner.

Block S220 recites: for each full-length target sequence identified, cutting out the full-length target sequence with a targeted cutting method. As shown in FIG. 8B, Block S220 functions to excise the full-length target sequences, in order to facilitate subsequent steps associated with tagging, fragmentation, and iterative processing to break down each full-length sequence into a set of sequence-able fragments that are easily assembled. In relation to the targeted cutting method, Block S220 preferably includes using CRISPR-associated endonucleases to excise the full-length target sequences. In variations, Block S220 uses a Cas9 endonuclease that produces blunt ends and/or sticky ends with or without fragment end repair associated with the endpoints of the full-length target sequences in a high efficiency manner, such that, after cutting, the target sequences do not self-ligate prematurely. In a specific example, as shown in FIG. 8B, Block S220 can include cutting out each of the full-length target sequences at PAM sites closest to, but beyond the initiating and terminating positions of each sequence, using a Cas9 endonuclease. Endonucleases (e.g., of gRNA complexes; used for digestion operations; etc.) and/or other suitable proteins used in and/or associated with (e.g., for fragments and /or other suitable components, ligating restriction enzyme sites corresponding to protein types described herein, etc.) Block S220 and/or other suitable processes described herein can be typified by and/or otherwise associated with protein type families including at least one of: cas, cpf, cas, cse, csy, csn, csd, cst, csh, csa, csm, cmr, other CRISPR-associated protein type families, BalI, BsrBI, HpaI, NruI, PsiI, PvuII, ScaI, SnaBI, AfeI, BsaBI, EcoRV, FspI, NaeI, PmeI, SfoI, SrfI, SwaI, and/or any other suitable protein types. However, in relation to blunt end formation and/or sticky end formation, Block S220 can additionally or alternatively use other RNA-guided endonucleases potentially able to generate blunt ends and/or sticky ends with or without end repair with high efficiency.

Additionally or alternatively, Block S220 can include implementing another targeted cutting method, which in variations includes use of any other restriction enzymes configured to target restriction sites (e.g., naturally-occurring restriction sites, synthetic restriction sites) near end points of the full-length target sequences. Such restriction enzymes can be configured to generate blunt and/or sticky ends (e.g., to induce pre-mature ligation), or can alternatively be configured to cooperate with other processing materials in any other suitable manner. However, Block S220 can be performed in any suitable manner.

Block S230 recites: generating an augmented full-length target sequence upon ligating a custom oligonucleotide sequence, including a first add-on target cutting site and a complete barcode sequence split by the first add-on target cutting site, onto the full-length target sequence. Block S230 can functions to support subsequent fragmentation steps in a manner that facilitates downstream assembly after amplification of fragments, by guaranteeing that each fragment generated has a portion of a barcode sequence that can be used to properly assemble the fragments into a reassembled sequence. Block S230 preferably includes ligating an oligonucleotide sequence having a single add-on target cutting site; however, Block S230 can alternatively include ligation of an oligonucleotide sequence having multiple add-on target cutting sites.

In Block S230, the first add-on target cutting site is preferably a site recognizable and/or targeted by CRISPR associated endonucleases (e.g. Cas9) , and in examples, can include a PAM site having one of the following sequences: 5'-NGA-3'; 5'-NGG-3'; 5'-TTN-3'; 5'-YTN-3'; and any other suitable PAM sequence. A specific example can include targeting microorganism target sequences of the set of nucleic acid components with gRNAs of gRNA complexes; generating full-length target sequence fragments based on processing a set of nucleic acid components with endonucleases (and/or other cutting-associated proteins; etc.) of the gRNA complexes; and ligating a set of custom nucleotide molecules (e.g., including cutting sites and identifier tags) with the full-length target sequence fragments to generate the augmented full-length target sequence fragments. Additionally or alternatively, the first add-on target cutting site can be a restriction digest site configured to be cut by any suitable restriction enzyme.

In Block S230, the complete barcode sequence is preferably a unique sequence that can be used to uniquely identify the full-length target sequence (e.g., microorganism target sequence; etc.). The complete barcode sequence can thus be randomly generated (e.g., computationally) such that it has no naturally-occurring analogue. Furthermore, the complete barcode sequence is preferably of a length that allows it to be identified, even after fragmentation in subsequent steps. Furthermore, the sequence is preferably designed to be of a length that reduces self-interference and/or interference with portions of the target sequence. In variations, the complete barcode sequence can include multiple identical portions (e.g., two identical portions sandwiching the first add-on target cutting site); however, the complete barcode sequence can alternatively include non-identical portions in a manner that enables downstream assembly. For instance, the barcode sequence can include a subsequence at a first side of the first add-on target cutting site and a reversed version of the subsequence at a second side of the first add-on target cutting site, thereby enabling down stream identification by way of the "opposing" subsequences of the barcode sequence. However, the complete barcode sequence can alternatively be configured or designed in any other suitable manner.

Block S230 can include implementing an end region (e.g., blunt end, sticky end) ligation protocol. In variations, the end region (e.g., blunt end, sticky end) ligation protocol can be a restriction cloning protocol. In a first specific example, the ligation protocol can implement a T3 DNA ligase (e.g., bacteriophage T3 DNA ligase) with appropriate buffer materials. In other examples, the ligation protocol can implement any other suitable ligase(s) or ligation protocol steps to ligate adaptor components at the cut region generated in Block S220.

Additionally or alternatively, Block S230 can implement end region (e.g., blunt end, sticky end) ligation improving steps (e.g., in terms of efficiency of ligation, etc.), including one or more of: increasing concentrations of inserts and/or ligases; performing ligation reactions in multiple steps (e.g., in a manner that reduces generation of concatemers); using longer incubation times; using DNA end repair enzymes and polynucleotide kinases, using reaction temperatures that are between the best temperature for DNA ligase activity and melting temperatures; dephosphorylating the vectors used; phosphorylating inserts used; reducing ATP concentration; using a polyethylene glycol (PEG)-rich ligation mixture; using lower concentration of monovalent cations in buffers; and any other suitable protocol step.

Furthermore, in Block S230, the ligation protocol can produce a sticky end to facilitate subsequent circularization of the linear sequence; however, the ligation protocol can alternatively produce an end region (e.g., blunt end, sticky end), and subsequent circularization steps can be configured to circularize linear sequences from blunted ends. However, Block S230 can be performed in any suitable manner.

Block S240 recites: circularizing the augmented full-length target sequence, which can function to form a circularized vector that can be cut in Block S250 in a manner that divides the complete barcode sequence into separate fragments of the full-length target sequence. Block S240 thus supports an iterative fragmentation and tagging protocol in Block S260 that allows the sequence of the original full-length target sequence to be retained, while attaching barcode sequences that facilitate downstream assembly in relation to fragment order and position within the full-length target sequence. In a specific example, Block S240 can include generating full-length target sequence fragments based on performing a fragmentation operation on the set of nucleic acid components; and generating a circularized augmented target sequence fragment including a custom nucleotide molecule of a set of custom nucleotide molecules, based on processing the custom nucleotide molecule with a full-length target sequence fragment of the full-length target sequence fragments.

Block S240 preferably implements a self-circularization protocol for circularization of the augmented full-length target sequence. In a first example, Block S240 can include combining the augmented full-length target sequence with DNA ligase buffer, DNA ligase (e.g., T4, but not intended to limit the invention), and nuclease-free water, followed by centrifugation and incubation (e.g., with shorter incubation times for sticky ends and longer incubation times for blunt ends and/or sticky ends). The efficiency of the self-circularization protocol (e.g., in terms of electrotransformation, etc.) can be improved by any one or more of: heat activation of DNA ligase, purification of DNA, increasing reaction time, addition of polyethylene glycol (PEG), and any other suitable step to improve circularization efficiency. However, Block S240 can alternative implement any other suitable circularization protocol using any other suitable ligase, any other suitable ligase buffer, any other suitable incubation time, any other suitable incubation temperature, and/or any other suitable process reagents and/or protocols. However, Block S240 can be performed in any suitable manner.

Block S250 recites: cutting the augmented full-length target sequence at a natural cutting site within the full-length target sequence and at the first add-on target cutting site, thereby generating a first sub-length target sequence and a second sub-length target sequence (and/or any suitable number of sub-length target sequence reviews; etc.), the first and the second sub-length target sequences associated with each other by inclusion of sequences that form the complete barcode sequence. Block S250 can function to generate a plurality of fragments (e.g., linear fragments) from the circularized augmented full length target sequence, in a manner that allows the sequence of the original full-length target sequence to be retained, while facilitating downstream assembly in relation to fragment order and position within the full-length target sequence. In a specific example, Block S250 can include generating sub-length target sequence fragments includes cutting the circularized augmented target sequence fragment at a cutting site of the custom nucleotide molecule and at a natural cutting site of the circularized augmented target sequence fragment. In another specific example (e.g., such as where identifier tags include complete barcode sequences split by add-on cutting sites), generating sub-length target sequence fragments can include, based on cutting the add-on cutting site: generating a first sub-length target sequence fragment associated with a first barcode portion of the complete barcode sequence; generating a second sub-length target sequence fragment associated with a second barcode portion of the complete barcode sequence; and determining a microbiome analysis based on the first and the second barcode portions (e.g., generating branched assemblies based on the barcode portions; reducing branched assemblies based on the barcode portions; etc.).

Similar to Block S220, Block S250 preferably includes using CRISPR-associated endonucleases to cut the circularized augmented full-length target sequence at the natural cutting site within the full-length target sequence and at the first add-on target cutting site. In variations, Block S250 uses a CRISPR associated endonucleases (e.g. Cas9) that produces blunt ends and/or sticky ends at each cutting site (e.g., the natural cutting site and the first add-on target cutting site) in a high efficiency manner, such that, after cutting, the fragmented sequences do not self-ligate or otherwise interfere prematurely. Cutting operations and/or other suitable processes of the method 200 (e.g., Block S220, Block S250) can include performing similar cutting operations (e.g., using same types of gRNA complexes, same times of CRISPR-association endonucleases, similar cutting operation protocols; etc.), different cutting operations (e.g., different types of gRNA complexes; etc.), and/or any combination of cutting operations and/or other suitable processes. In a specific example, as shown in FIG. 8B, Block S250 can include cutting both the natural site and the add-on target cutting site using Cas9 endonucleases. In another specific example, Block S250 can include cutting the cutting sites of the set of custom nucleotide molecules (e.g., ligated to full-length target sequence fragments; etc.) with second gRNA complexes including second endonucleases and second gRNAs associated with the cutting sites (e.g., where first gRNA complexes including first endonucleases and first gRNAs are used to perform cutting associated with Block S220). However, in relation to blunt end and/or sticky end formation, Block S250 can additionally or alternatively use other RNA-guided endonucleases potentially able to generate blunt ends and/or sticky ends with high efficiency.

Alternatively, Block S250 can include implementing another targeted cutting method, which in variations includes use of any other restriction enzymes configured to target the natural cutting site and the first add-on cutting site. Such restriction enzymes can be configured to generate blunt or sticky ends (e.g., to induce pre-mature ligation), or can alternatively be configured to cooperate with other processing materials in any other suitable manner. For instance, Block S250 can include using a first cutting method for the natural cutting site and a second cutting method for the add-on target cutting site, where the first and the second cutting methods may or may not be identical to each other. Furthermore cutting of the natural cutting site and the add-on target cutting site can occur substantially contemporaneously or simultaneously; alternatively, cutting of the natural cutting site and the add-on target cutting site can occur at different times (e.g., in stages). However, Block S250 can be performed in any suitable manner.

Block S260 recites: iteratively subdividing the first and the second sub-length target sequences according to Blocks S230 through S250 (and/or other portions of the method 200), until a final generation of final sub-length target sequences (e.g., sequence fragments; etc.) is reached (e.g., where performing sequencing operations can be based on the final sub-length target sequence fragments; etc.), where each of the final generation of sub-length target sequences has a length below a threshold sequencing length and/or includes a subportion of a set of complete barcode sequences implemented in Block S230 and iterations of Block S260. Block S260 functions to iteratively fragment the full-length target sequence portions until the final iteration of fragments has a characteristic size sequence-able by an appropriate sequencing platform, while ensuring that each fragment has identifiers/barcode portions that identify the fragments position within the full-length target sequence. In Block S260, each new custom oligonucleotide sequence used preferably has a unique barcode sequence separated by a cutting site in order to facilitate subsequent assembly steps.

Figure 9A:
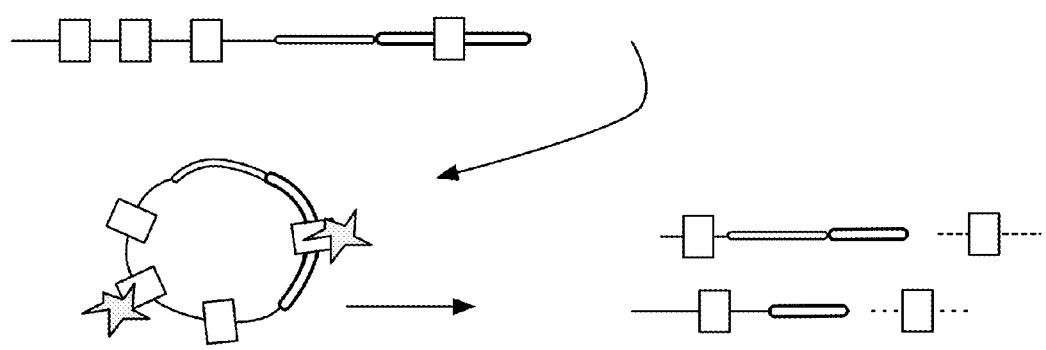
FIGS. 9A-9B depict variations of a portion of a second method for sequencing and assembly of full-length target sequences.
Figure 9B:
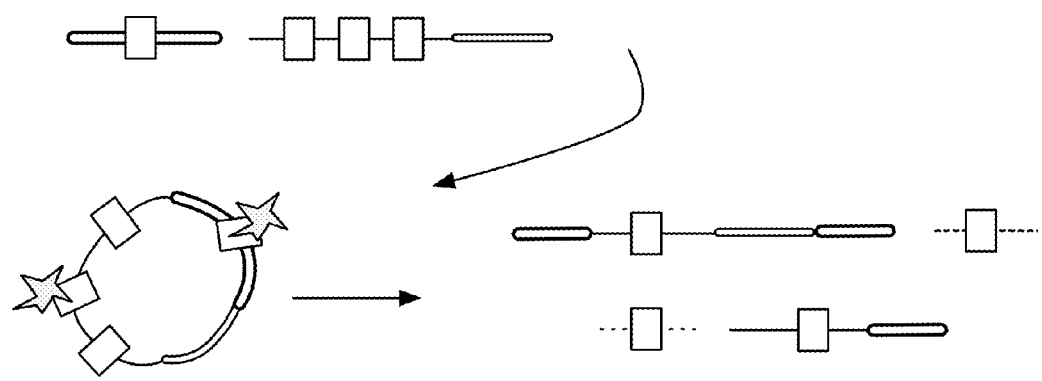

For each iteration (e.g., of Blocks S230-S250), ligation of the custom oligonucleotide sequence can occur at the end of a linearized fragment closest to the natural cutting site, or can occur at the end of a linearized fragment closest to the add-on cutting site ligated onto the fragment during the previous iteration (e.g., of Blocks S230-S250). As such, portions of the set of complete barcode sequences can be appended onto each other, as shown in FIG. 9A; alternatively, portions of the set of complete barcode sequences can alternatively be spaced apart by sub-portions of the original full-length barcode sequence, as shown in FIG. 9B, such that sequential barcode portions are not directly appended to each other.

At the final iteration, fragment lengths in Block S260 are preferably on the order of 200-400 base pairs (bp) in length, including the barcode sequence sub-portions, and in specific examples, can be on the order of 30 bp in length for sequencing using an Illumina™ platform. However, fragment lengths at the final iteration of Block S260 can alternatively be of any other suitable length, in relation to sequencing using any other suitable platform. Block S260 can, however, be implemented in any other suitable manner.

Block S270 recites: preparing each of the final generation of sub-length target sequences for a sequencing operation, which functions to add adaptor sequences (e.g., Nextera adaptors, etc.) to the fragments produced by Block S260, in preparation for amplification, sequencing, and assembly. The adaptor sequences implemented Block S270 are preferably configured for the sequencing platform used in Block S280, and in variations, can include one or more of the following components: a forward index sequence (e.g., corresponding to an Illumina forward index for MiSeq/NextSeq/HiSeq platforms), or a reverse index sequence (e.g., corresponding to an Illumina reverse index for MiSeq/NextSeq/HiSeq platforms), a forward barcode sequence or a reverse barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region, and any other suitable adapter component.

Preparation can additionally or alternatively include any embodiments, variations, and examples of preparation protocols, as described in U.S. application Ser. No. 14/593,424 titled "Method and System for Microbiome Analysis" and filed on 9 Jan. 2015, or U.S. application Ser. No. 15/097,862 titled "Method and System for Microbiome-Derived Diagnostics and Therapeutics for Neurological Health Issues" and filed on 13 Apr. 2016, each of which is incorporated in its entirety herein by this reference. However, Block S270 can be performed in any suitable manner.

Block S280 recites: amplifying and sequencing each of the sub-length target sequences according to the sequencing operation, which functions to amplify outputs of Block S270 for subsequent sequencing and analysis (e.g., to characterize microbiome aspects of biological samples). Block S280 preferably includes using amplification with a single primer/primer set that is associated with the adapter used in Block S270. As such, Block S280 involves amplification in a manner that reduces or entirely eliminates primer interference factors (e.g., self-dimer formation, primer-dimer formation), and reduces amplification bias. Thus, the primer/primer set can be selected to prevent or minimize amplification bias effects, as well as configured to amplify nucleic acid regions/sequences (e.g., of a 16S rRNA gene region, a 18S rRNA gene region, a ITS region, etc.) that are informative taxonomically, phylogenetically, for diagnostics, and/or for any other suitable purpose. However, any suitable number of primers and/or primer types can be used in Block S280 and/or other suitable portions.

In Block S280, amplifying preferably includes one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and/or any other suitable amplification technique.

Additionally or alternatively, Block S280 can implement any other step configured to facilitate processing, amplification, and sequencing steps subsequent to amplification, some embodiments, variations, and examples of which are described in as described in U.S. application Ser. No. 14/593,424 titled "Method and System for Microbiome Analysis" and filed on 9 Jan. 2015, or U.S. application Ser. No. 15/097,862 titled "Method and System for Microbiome-Derived Diagnostics and Therapeutics for Neurological Health Issues" and filed on 13 Apr. 2016, each of which is incorporated in its entirety herein by this reference.

In specific applications, the method 200 (and/or 100) can ultimately be applied to generation of detection and/or diagnostic tests that are based on sample processing, target amplification, and sequencing in an efficient manner. In specific applications, the diagnostic tests can be associated with at least one or more neurological health conditions, one or more autoimmune condition, one or more endocrine system conditions, one or more mental health conditions, one or more locomotor system conditions, one or more metabolic (associated) disease conditions, one or more cardiovascular disease conditions, one or more cutaneous conditions, one or more sexually transmitted diseases, one or more dental health conditions, one or more gastrointestinal health conditions, and/or any other suitable condition, embodiments, variations, and examples of which are described in U.S. application Ser. No. 14/919,614 filed on 21 Oct. 2015, U.S. application Ser. No. 15/097,862 filed on 13 Apr. 2016, U.S. application Ser. No. 15/098,027 filed on 13 Apr. 2016, U.S. application Ser. No. 15/098,248 filed on 13 Apr. 2016, U.S. application Ser. No. 15/098,236 filed on 13 Apr. 2016, U.S. application Ser. No. 15/098,222 filed on 13 Apr. 2016, U.S. application Ser. No. 15/098,204 filed on 13 Apr. 2016, U.S. application Ser. No. 15/098,174 filed on 13 Apr. 2016, U.S. application Ser. No. 15/098,110 filed on 13 Apr. 2016, U.S. application Ser. No. 15/098,081 filed on 13 Apr. 2016, and U.S. application Ser. No. 15/098,153 filed on 13 Apr. 2016, which are herein incorporated in their entireties by this reference. However, Block S280 can be performed in any suitable manner.

Block S290 recites: re-assembling the full-length target sequence based upon the set of complete barcode sequences. Block S290 functions to efficiently assemble the amplified and sequenced fragments produced by the iterative process of Block S260, based upon the portions of the set of complete barcode sequences included in each fragment outputted from Block S260. In more detail, given that complete barcode sequences are divided at each iteration of Block S260, Block S290 can include iterative reassembly of pairs of fragments, based on their respective associated barcode portions that form a complete barcode sequence of the set of barcode sequences, until the full-length target sequence is re-assembled. However, Block S290 can include re-assembling the full-length target sequence in any other suitable manner.

5. Method 300.

Figure 10A:
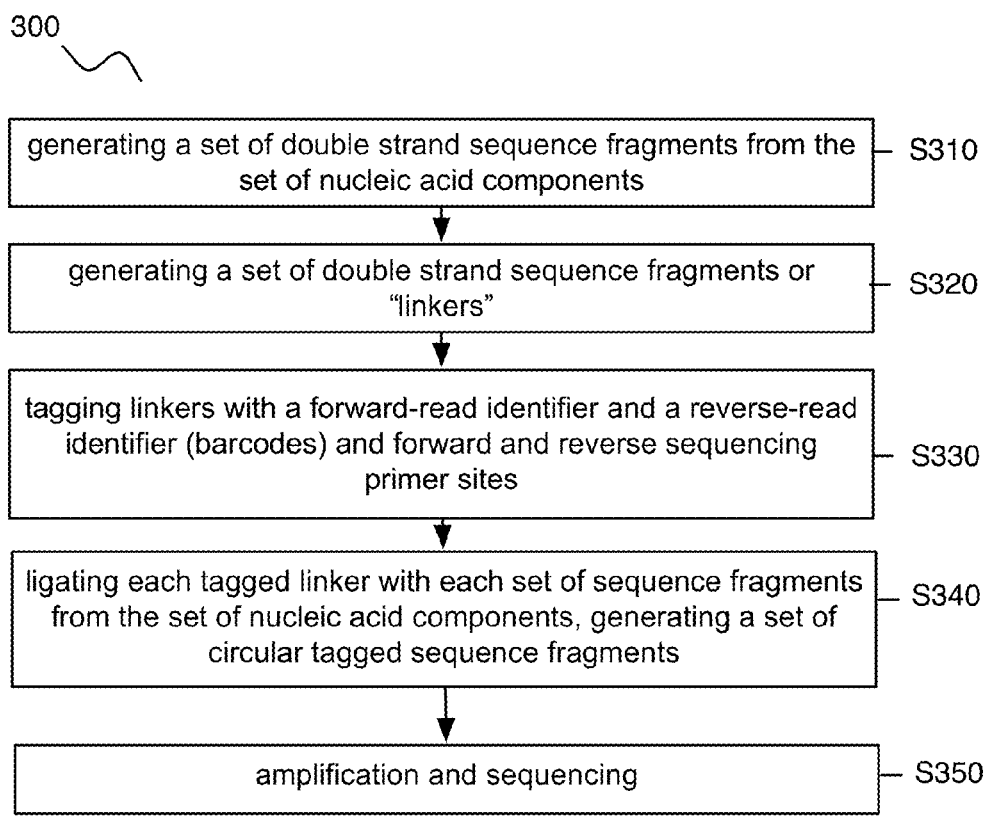
FIGS. 10A-10C depict embodiments of a third method for sequencing and assembly of full-length target sequences.
Figure 10B:
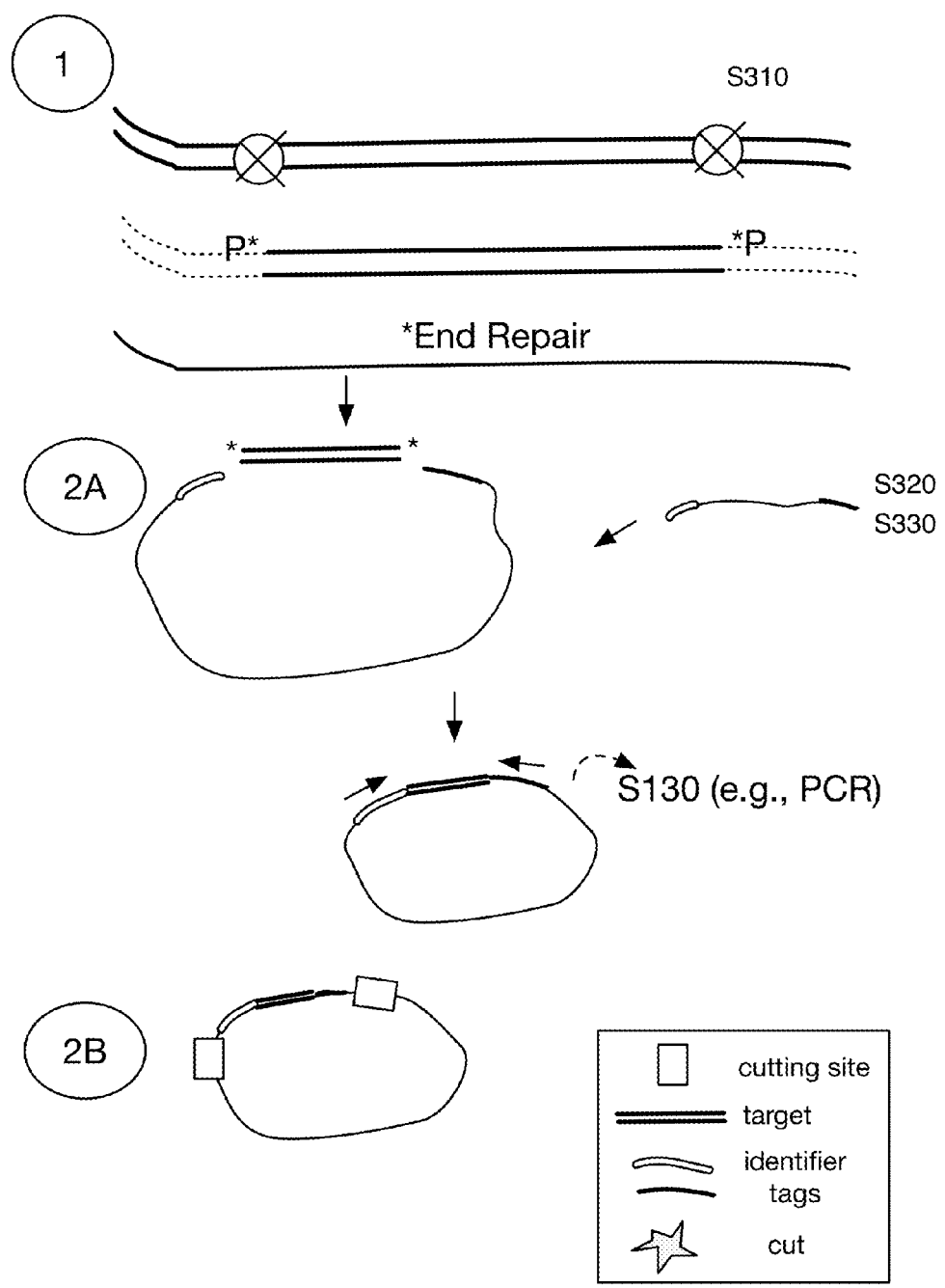
Figure 10C:
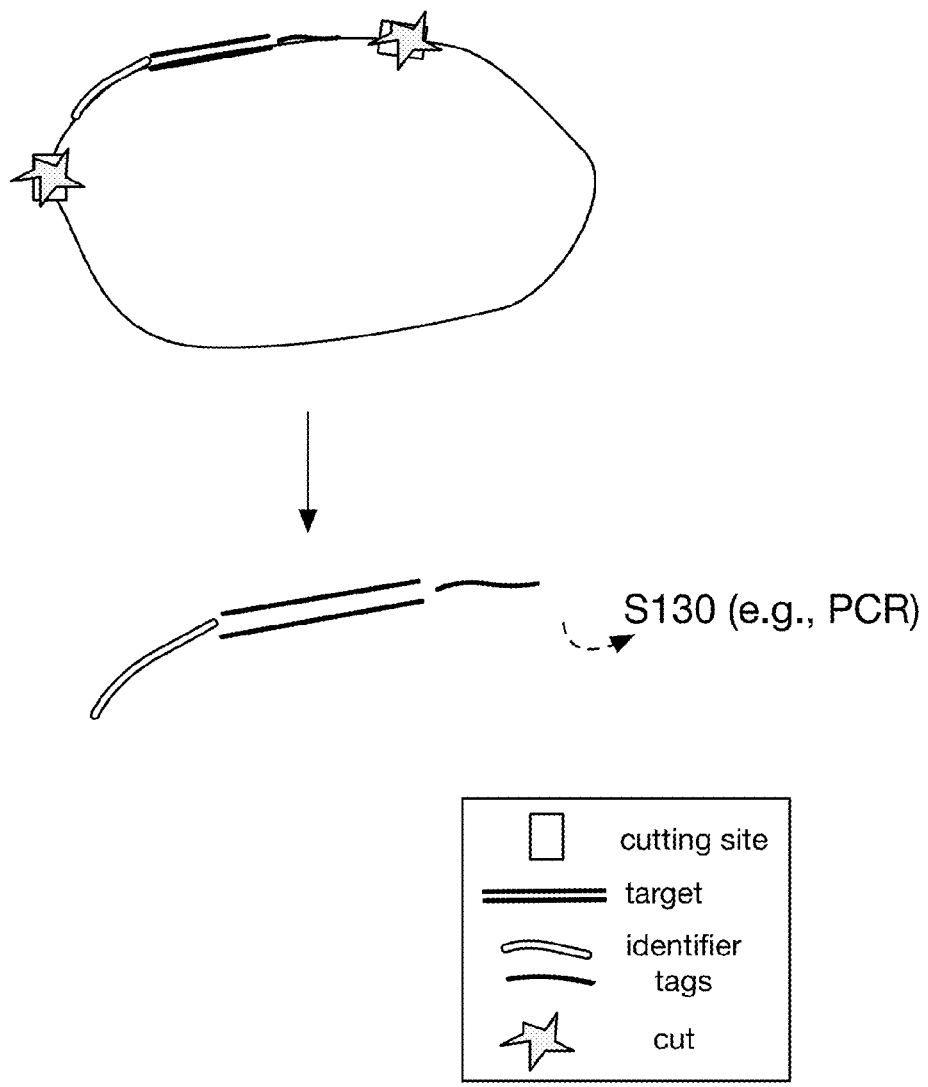
Figure 11:
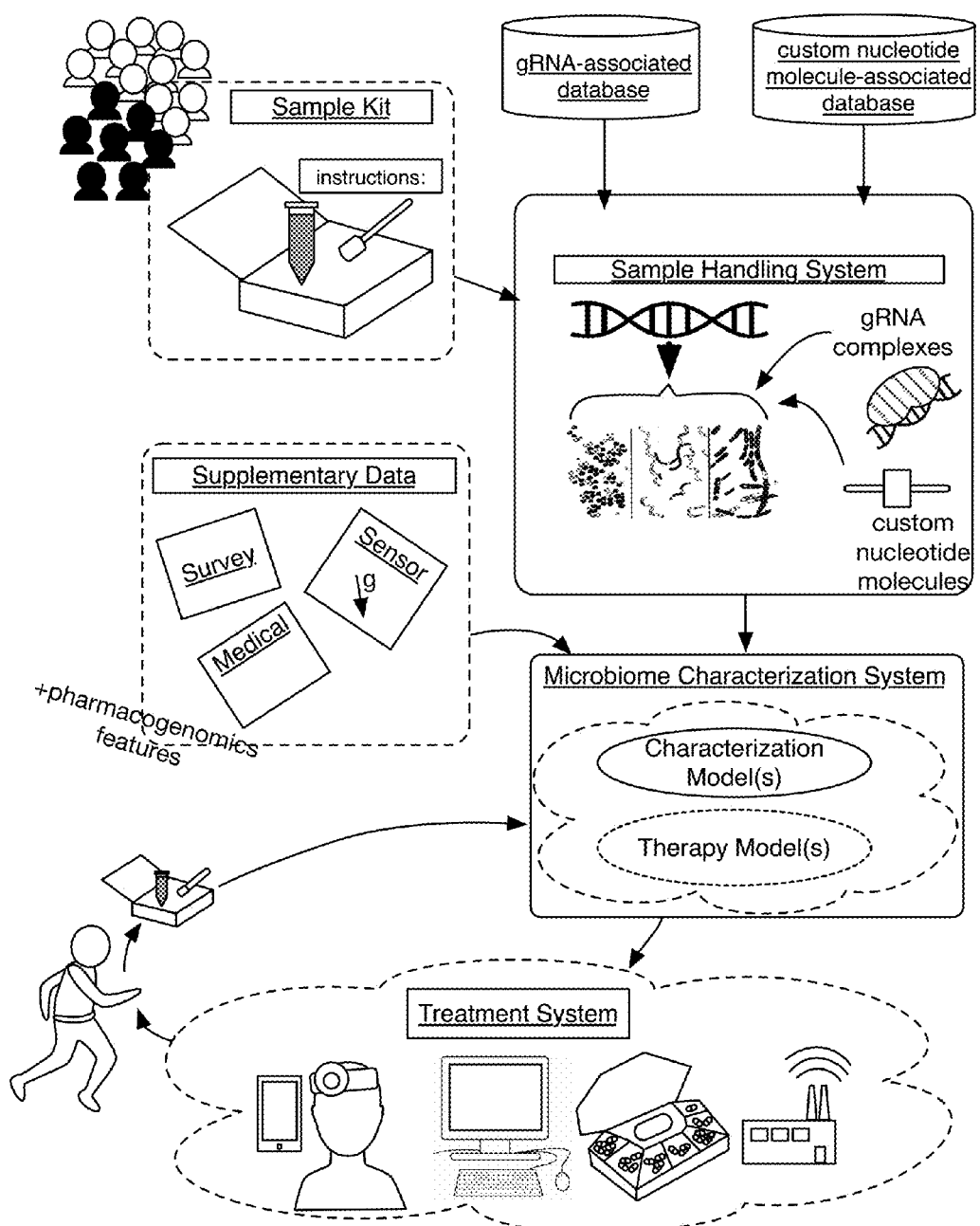
FIG. 11 depicts a schematic representation of embodiments of a system for fragment assembly and sequence identification.

As shown in FIGS. 10A-10C, embodiments of the method 100 can additionally or alternatively include portions of the method 300 (e.g., which can be implemented as a variation of Block S120; etc.) for facilitating improved assembly and sequencing of fragments of nucleic acid sequences. In more detail, the embodiments of the method 30 can include: generating a set of double strand sequence fragments from the set of nucleic acid components 310; generating a set of double strand sequence fragments (e.g., double strand fragment links linkers; etc.) which can be of any sequence and any length 320; tagging the linkers with a forward-read identifier and a reverse-read identifier and forward and reverse sequencing primer sites 330; ligating each tagged linker with each set of sequence fragments from the set of nucleic acid components, generating a set of circular tagged sequence fragments 340; and performing further amplification and sequencing with the set of circular tagged sequence fragments 350.

Block 310 recites: generating a set of double strand sequence fragments from the set of nucleic acid components, including generating a set of site guided RNAs (gRNAs) configured to target sequences of the set of targets, which functions to guide endonuclease activity in downstream steps associated with blunt end and/or sticky end formation and ligation, in relation to sequence positions of the set of targets. In relation to generating the set of gRNAs, Block 310 can include implementing an algorithm that selects gRNA sequences that have little-to-no tendency to form secondary structures and takes into account tendencies of candidate gRNAs to self-bind. The gRNA design and selection algorithm can thus rank candidate gRNA sequences based upon the set of genomic targets desired for amplification, based upon a set of gRNA design factors, based upon minimizing off-target activity/maximizing on-target activity (e.g., with analysis and selection of identification of potential protospacer sequences around target sites), and based upon any other suitable design factor.

In variations, the set of gRNA design factors for selection of the set of gRNAs can include one or more of: a folding energy factor (e.g., associated with tendency to form secondary structures); a hybridization factor (e.g., associated with tendency to interact/interfere with other gRNAs in the mix); a GC content factor; a nucleotide run factor; a first binding energy factor (e.g., associated with a first subset of base pairs); a second binding energy factor (e.g., associated with a second subset of base pairs, if criteria associated with the first binding energy factor is satisfied); a GC clamp factor; and any other suitable factor. In variations, the algorithm for selection/generation of the set of gRNAs can be adapted from and/or analogous to method for multiplex primer design described in U.S. application Ser. No. 15/240,919 titled "Method and System for Multiplex Primer Design" and filed on 18 Aug. 2016, which is herein incorporated in its entirety by this reference.

In a specific example, the gRNA generation algorithm can implement criteria associated with a folding energy factor, a hybridization factor; a GC content factor; a runs factor; a first binding energy factor (e.g., associated with the first 13 bps of a gRNA); a second binding energy factor (e.g., associated with a remainder of 7 bps, if criteria associated with the first binding energy factor is satisfied).

The set of gRNAs can be designed to target positions (e.g., positions associated with 16S rRNA gene regions, positions associated with 18S rRNA gene regions, positions associated with ITS regions, etc.) associated with nucleic acid sequences of the same organism and/or associated with different organisms. Block Siio can be used to generate a single gRNA, a pair of gRNAs, and/or can be used to generate more than two gRNAs (e.g., 16S rRNA and 18S rRNA gRNAs) to be used to facilitate subsequent targeting, cutting, ligating, and amplification steps. Block 310 can, however, be implemented in any other suitable manner.

Block 320 recites: generate a set of double strand sequence fragments (e.g., double strand fragment linkers, etc.), where, this linker sequence can be obtained preferentially by de novo synthesis (or any other suitable source or method), and where the linker sequence can be selected from one or more of the following groups: random sequence fragments, sequence fragment including PAM sites or any other restriction enzyme site, plasmids, and/or any other source of sequence fragment available.

In a variation of Block 320, linkers can include a restriction enzyme, PAM site and/or other suitable components, that could be useful for implementation of 340, for isolation of only sequence of interest without linker sequence (e.g., as shown in FIG. 10C).

Additionally or alternatively, in a variation of 320, linkers can be synthesized in a manner where one strand is synthesized directly with a required tag for downstream steps (e.g., with a forward-read identifier and a reverse-read identifier, with forward and reverse sequencing primer sites). Additionally or alternatively, linkers can be hybridized with a complementary synthesized single strand. Additionally or alternatively, PCR can be implemented in relation to double strand linker generation. However, Block 320 can be performed in any suitable manner.

Block 330 recites: tagging linkers with a forward-read identifier and a reverse-read identifier (e.g., barcodes) and forward and reverse sequencing primer sites (e.g., where the double strand fragment linkers include forward-read identifiers, reverse-read identifiers, forward sequencing primer sites, reverse sequencing primer sites, and/or other suitable components; etc.), using a ligase enzyme to join linker sequences obtained in 320 and target barcode and primers as required. Tagging can be performed in a manner analogous to the embodiments, variations, and/or examples of the method portions described above. However, Block 330 can be performed in any suitable manner.

Block 340 recites: ligating each tagged linker with each set of sequence fragments from the set of nucleic acid components (e.g., generating the augmented full-length target sequence fragments based on ligating the double strand fragment linkers with full-length target sequence fragments; etc.); generating a set of circular tagged sequence fragments (e.g., where joining of specific tagged linker and double strand sequence fragments from the set of nucleic acid components can be made by mixing both components with a ligase enzyme; etc.); and/or obtaining a set of circular tagged sequence fragments for each set of sequence fragments from the set of nucleic acid components. Additionally or alternatively, ligation processes can be implemented in manners analogous to the embodiments, variations, and/or examples of the method portions described above. However, Block 340 can be performed in any suitable manner.

Block 350, includes using amplification and sequencing (paired end) circular tagged sequenced fragment obtained in S340, where, amplification techniques include: PCR, CRISPR/CAS, or any other suitable technique; and any other suitable sequencing technique available, as described in the embodiments, variations, and examples of the methods described above. However, Block 350 can be performed in any suitable manner.

Variations of the above method 200 can be combined with method 100 in any suitable manner to modulate computational difficulty and/or extensiveness of wet lab processing techniques. For instance, fewer iterations of Block S260 can be implemented to generate a set of barcoded fragments having fragment lengths larger than typical for sequencing using an appropriate platform; however, at this stage, the method can include fragmentation as in the method 100, with more extensive computations in relation to assembly. The methods 100, 200 can, however, be combined in any other suitable manner.

Variations of the above method 300 can be combined with method 200 and 100, in any suitable manner to modulate computational difficulty and/or extensiveness of wet lab processing techniques.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for improving fragment assembly and sequence identification in relation to a set of microorganisms, the method comprising:
   collecting a sample including a set of nucleic acid components associated with the set of microorganisms;
   generating a set of tagged sequence fragments based on a set of identifier tags and a set of sequence fragments derived from the set of nucleic acid components of the sample, wherein generating the set of tagged sequence fragments comprises:
      targeting, with guide RNAs (gRNAs) of gRNA complexes, microorganism target sequences of the set of nucleic acid components at identified sequence positions;
      cutting the set of nucleic acid components in relation to the microorganism target sequences with endonucleases of the gRNA complexes, thereby generating the set of sequence fragments;
      ligating the set of identifier tags to the set of sequence fragments, thereby generating augmented sequence fragments, wherein each identifier tag of the set of identifier tags comprises a complete barcode sequence comprising a first barcode portion and a second barcode portion separable by cutting of a cutting site; and
      generating the set of tagged sequence fragments based on circularization of the augmented sequence fragments and the cutting of the cutting sites to separate the first barcode portions and the second barcode portions;
   sequencing the set of tagged sequence fragments;
   generating a set of branched assemblies corresponding to candidate sequence fragments, based on the identified sequence positions and the set of identifier tags associated with the sequenced set of tagged sequence fragments, wherein each branched assembly of the set of branched assemblies comprises a set of branches distributed across a set of nodes, wherein generating the set of branched assemblies comprises:
      detecting the first barcode portions and the second barcode portions of the set of identifier tags at the sequenced set of tagged sequence fragments; and
      generating the set of branches distributed across the set of nodes based on the detected first barcode portions and the second barcode portions in relation to the complete barcode sequences;
   implementing a threshold criterion to reduce the set of branched assemblies to a set of branch-reduced assemblies; and
   identifying a set of microorganism sequences corresponding to the set of branch-reduced assemblies.

2. The method of claim 1, wherein implementing the threshold criterion comprises, for the each branched assembly of the set of branched assemblies, applying the threshold criterion for each node coupled to branches of the set of branches to generate an unbranched assembly.

3. The method of claim 1, wherein each node of the set of nodes of the set of branched assemblies corresponds to a microorganism sequenced fragment comprising a length, an initiating position, and a terminating position, wherein a connection between adjacent nodes of the set of nodes corresponds to a candidate continuity between a plurality of microorganism sequenced fragments, and wherein identifying the set of microorganism sequences comprises identifying the set of microorganism sequences based on the length, the initiating position, the terminating position, and the connection between adjacent nodes.

4. The method of claim 1, wherein each node of the set of nodes corresponds to a position along an assembled microorganism sequence, wherein each branch of the set of branches corresponds to a microorganism sequenced fragment comprising an initial position corresponding to an upstream node and a terminating position corresponding to a downstream node, and wherein identifying the set of microorganism sequences comprises identifying the set of microorganism sequences based on the initial position, the terminating position, and the position along the assembled microorganism sequence.

5. The method of claim 1, wherein the threshold criterion comprises a similarity coefficient associated with similarity between the set of branched assemblies and an additional set of branched assemblies corresponding to an additional sample, and wherein implementing the threshold criterion comprises implementing the similarity coefficient for the set of branches and the set of nodes to reduce the set of branched assemblies to the set of branch-reduced assemblies.

6. The method of claim 5, wherein the similarity coefficient comprises at least one of: a Tanimoto Coefficient, a Jaccard distance parameter, a Sorensen similarity index, a simple matching coefficient, a Mountford's index of similarity, a Hamming distance, a Dice's coefficient, a Tversky index, and a Mutual information parameter.

7. The method of claim 1, wherein the set of nucleic acid components comprise target sequence regions associated with the set of microorganisms, wherein the target sequence regions comprise target sequences for identification of a specific target that include at least one of a 16S rRNA sequence region, 18S rRNA sequence region, and an ITS sequence region, and wherein generating the set of branched assemblies comprises generating the set of branched assemblies for facilitating the improved fragment assembly and the sequence identification in relation to the target sequence regions.

8. The method of claim 7, wherein the target sequence regions comprise a polymorphic or variable region of a specific target sequence region, wherein the polymorphic region can be used for identification, selection and/or differentiation of a single microorganisms.

9. The method of claim 8, wherein the specific target sequence region comprises: 16S sequence region, 18S sequence region, ITS region, and any sequence region that can be used for identification, selection and/or differentiation of a single microorganisms.

10. The method of claim 8, wherein the target sequence regions comprise at least one polymorphic region of the 16S rRNA sequence region, wherein the at least one polymorphic region comprises one or more of: V1, V2, V3, V4, v5, v6, v7, v8, and v9.

11. The method of claim 1, further comprising:
   generating a graphical representation of the set of branched assemblies based on the set of branches and the set of nodes;
   presenting the graphical representation of the set of branched assemblies;
   collecting a user input associated with the set of branched assemblies in response to presenting the graphical representation of the set of branched assemblies, wherein implementing the threshold criterion comprises implementing the threshold criterion to reduce the set of branched assemblies to the set of branch-reduced assemblies based on the user input.

12. The method of claim 1, wherein each branched assembly of the set of branched assemblies corresponds to a set of candidate assembled sequences comprising de-branched assembled sequences, and wherein the method further comprises defining an operational microorganism taxonomic unit comprising the de-branched assembled sequences.

13. The method of claim 1, wherein the endonucleases of the gRNA complexes comprise Cas9 endonucleases.

14. The method of claim 1, wherein the complete barcode sequences comprise unique complete barcode sequences operable to uniquely identify the microorganism target sequences.

* * * * *